(12) United States Patent
Buechler et al.

(10) Patent No.: US 6,777,190 B1
(45) Date of Patent: *Aug. 17, 2004

(54) CROSSTALK INHIBITORS AND THEIR USES

(75) Inventors: Kenneth F. Buechler, San Diego, CA (US); Richard R. Anderson, Encinitas, CA (US); Theodore T. Lee, Rancho Santa Fe, CA (US); Gunars E. Valkirs, Escondido, CA (US)

(73) Assignee: Biosite, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/241,061

(22) Filed: May 11, 1994

Related U.S. Application Data

(63) Continuation of application No. 08/156,671, filed on Nov. 23, 1993, now abandoned, which is a continuation of application No. 07/867,723, filed on Apr. 7, 1992, now abandoned, which is a continuation-in-part of application No. 07/683,456, filed on Apr. 10, 1991, now abandoned.

(51) Int. Cl.$^7$ ...................... A61K 39/395; G01N 33/53; C07K 16/00
(52) U.S. Cl. ...................... 435/7.1; 435/7.92; 435/7.93; 436/518; 436/501; 530/387.1; 424/178.1
(58) Field of Search ................................. 435/7.1, 7.92, 435/7.93, 964, 947, 973, 975; 436/501, 518, 536, 543, 547

(56) References Cited

U.S. PATENT DOCUMENTS

| | | | |
|---|---|---|---|
| 3,879,262 A | 4/1975 | Schuurs et al. | ............... 195/63 |
| 4,980,457 A | 12/1990 | Jansen et al. | ............... 530/391 |
| 4,981,979 A | 1/1991 | Sivam | ....................... 548/545 |
| 5,068,227 A | 11/1991 | Weinshenker | |

FOREIGN PATENT DOCUMENTS

| | | |
|---|---|---|
| EP | 0113318 | 7/1984 |

OTHER PUBLICATIONS

Christiaansen et al., J. Imm. Meth. 74 pp 229–239 (1984).*
Lin et al Biochem. Pharm. 41 pp 789–795 Mar. (1991).*
AldrichCatalogue 1984–1985 pp 51–692.*
J: Meth. Enz. 91 pp 580–609 (1983).*
Erlanger Meth. Enz. 70 pp 85–103.*
Marini et al., J. Imm. Meth. , vol. 120, pp57–63 (1989) "A simple method for increasing hapten immunogenicity by a specific structural modification of the carrier".*
Kinoshita et al., "Enzyme Immunoassay for Captopril," *Journal of Pharmaceutical Sciences* 75:711–713 (1986).
Pastor et al, "3–(4–Hydroxyphenylthio)pyrrolidine–2,5–diones," *J. Heterocycle Chem*. 22:1195–1197 (1985).
Hosada et al., "The Specificity of Enzyme Immunoassay for Plasma 11–Deoxycortisol", Chemical and Pharmaceutical Bulletin, vol. 31, pp. 3595–3600 (1983).
E. T. Maggio, "Enzyme–Immunoassay," CRC Press, Inc. pp. 71–104 (1987).
Kitagawa et al., "Enzyme Coupled Immunoassay of Insulin Using a Novel Coupling Reagent," Journal of Biochemistry, vol. 79, pp. 233–236, (1976).
Lin et al., "Bivalent ACTH Antagonists: Influence of Peptide and Spacer Components on Potency Enhancement", Biochemical Pharmacology, vol. 41, No. 5, pp. 789–795 (1991).
Van Weeman et al., "Enzyme Immunoassay of Hormones", Scand. J. Immunol., vol. 8, Suppl. 7, pp. 73–88 (1978).

* cited by examiner

*Primary Examiner*—Andrew Wang
(74) *Attorney, Agent, or Firm*—Foley & Lardner LLP; Richard J. Warburg

(57) ABSTRACT

Assay for detecting the amount or presence of target ligand in a sample. The assay includes a ligand analogue conjugate having a linkage site and a binding site, a ligand receptor, and a sample. The assay includes the steps of providing at least one crosstalk inhibitor. This inhibitor, under assay conditions, competes with the linkage site of the ligand analogue conjugate for binding to the ligand receptor, and does not compete with the binding site of the ligand analogue conjugate for binding to the ligand receptor. In the invention, the assay is performed for the target ligand in the presence of a sufficient amount of the crosstalk inhibitor to reduce the amount of binding of the linkage site of the ligand analogue conjugate to the ligand receptor. The invention also features a method for identifying crosstalk inhibitors, and the crosstalk inhibitors themselves.

11 Claims, 6 Drawing Sheets

(CCM)

CROSSTALK INHIBITORS AND THEIR USES

Figure 1A:
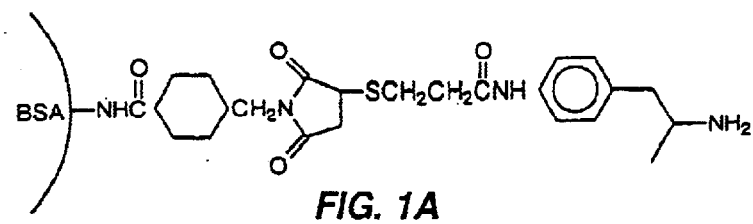
Figure 1B:
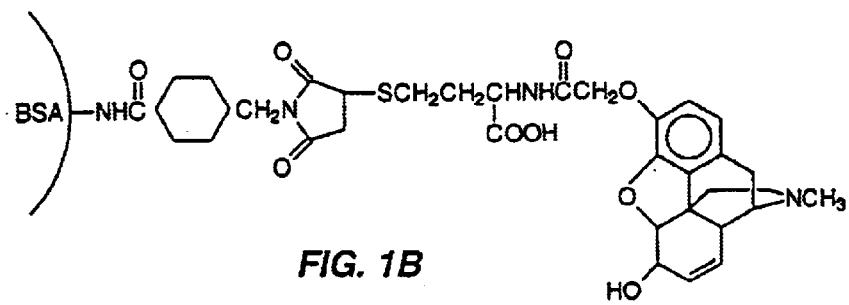

This application is a continuation of application Ser. No. 07/867,723, filed Apr. 7, 1992.

This application is a continuation of application Ser. No. 08/156,671, filed Nov. 23, 1993.

This application is a continuation-in-part of App. Ser. No. 07/683,456, filed Apr. 10, 1991, now abandoned from which priority is claimed.

FIELD OF THE INVENTION

This invention is in the field of assays, including immunoassays, for the detection of selected analytes in a fluid sample.

BACKGROUND OF THE INVENTION

As used herein, the term "ligand-receptor assay" refers to an assay for an analyte which may be detected by the formation of a complex between a ligand and a ligand receptor which is capable of specific interaction with that ligand. The ligand may be the analyte itself or a substance which, if detected, can be used to infer the presence of the analyte in a sample. In the context of the present invention, the term "ligand", includes haptens, hormones, antigens, antibodies, deoxyribonucleic acid (DNA), ribonucleic acid (RNA), metabolites of the aforementioned materials and other substances of either natural or synthetic origin which may be of diagnostic interest and have a specific binding partner therefor, i.e., the ligand receptor of the ligand-receptor assay. In the context of the present invention the term "ligand receptor" includes materials for which there is a specific binding partner, i.e., the ligand of the ligand-receptor assay. Those skilled in the art will appreciate that the analyte of interest is a member of a specific binding pair and may be either a ligand receptor or a ligand depending upon assay design.

Ligand-receptor assays are generally useful for the in vitro determination of the presence and concentration of ligands in body fluids, food products, animal fluids, and environmental samples. For example, the determination of specific hormones, proteins, therapeutic drugs, and toxic drugs in human blood or urine has significantly improved the medical diagnosis of the human condition. There is a continuing need for simple, rapid, non-instrumental assays for the qualitative, semi-quantitative, and quantitative determination of such ligands in a sample. In many situations, such assays need to be simple enough to be performed and interpreted by non-technical users. In addition, there has existed an unmet need to determine the presence and concentration of multiple ligands in a single assay. For example, the need exists for a rapid analytical tool to determine, in the emergency rooms of hospitals, the presence of the multiple drugs of abuse.

Ligand-receptor assays rely on the binding of ligands by ligand receptors to determine the concentration of ligands in a sample. Ligand-receptor assays can be described as either competitive or non-competitive. Non-competitive assays generally utilize ligand receptors in substantial excess over the concentration of ligand to be determined in the assay. Sandwich assays, in which the ligand is detected by binding to two ligand receptors, one ligand receptor labeled to permit detection and the second ligand receptor frequently bound to a solid phase to facilitate separation from unbound reagents, such as unbound labeled first ligand receptor, are examples of non-competitive assays. Competitive assays generally involve ligand from the sample, a ligand analogue labeled to permit detection, and the competition of these species for a limited number of binding sites provided by the ligand receptor. Those skilled in the art will appreciate that many variations of this basic competitive situation have been previously described and will not be discussed in detail herein except where pertinent to the general objectives of this invention. Examples of ligands which are commonly measured by competitive ligand-receptor assays include haptens, hormones and proteins. Antibodies that can bind these classes of ligands are frequently used in these assays as ligand receptors.

Competitive ligand-receptor assays can be further described as being either homogeneous or heterogeneous. In homogeneous assays all of the reactants participating in the competition are mixed together and the quantity of ligand is determined by its effect on the extent of binding between ligand receptor and labeled ligand analogue. The signal observed is modulated by the extent of this binding and can be related to the amount of ligand in the sample. U.S. Pat. No. 3,817,837 describes such a homogeneous, competitive immunoassay in which the labeled ligand analogue is a ligand-enzyme conjugate and the ligand receptor is an antibody capable of binding to either the ligand or the ligand analogue. The binding of the antibody to the ligand-enzyme conjugate decreases the activity of the enzyme relative to the activity observed when the enzyme is in the unbound state. Due to competition between unbound ligand and ligand-enzyme conjugate for antibody binding sites, as the ligand concentration increases the amount of unbound ligand-enzyme conjugate increases and thereby increases the observed signal. The product of the enzyme reaction may then be measured kinetically using a spectrophotometer.

In general, homogeneous assay systems require both an instrument to read the result and calibration of the observed signal by separate tests with samples containing known concentrations of ligand. The development of homogeneous assays has dominated competitive assay research and has resulted in several commercially available systems. Such systems are not, however, capable of providing results for the determination of multiple ligands in a sample in a single-test format not requiring complex instrumentation.

Heterogeneous, competitive ligand-receptor assays require a separation of bound labeled ligand or receptor from the free labeled ligand or receptor and a measurement of either the bound or the free fraction. Methods for performing such assays are described in U.S. Pat. Nos. 3,654,090, 4,298,685, and 4,506,009. Such methods, however, are not capable of providing semi-quantitative or quantitative results for the determination of ligands in a sample without using additional tests to calibrate the assay response.

The need for ligand-receptor assays that can be performed without the use of complex instrumentation has led to the development of immunoassays that are simple to perform and result in a response that can be visually interpreted. U.S. Pat. Nos. 4,125,372, 4,200,690, 4,246,339, 4,366,241, 4,446,232, 4,477,576, 4,496,654, 4,632,901, 4,727,019, and 4,740,468 describe devices and methods for ligand-receptor assays that develop colored responses for visual interpretation of the results. While such devices provide simple formats for the visual interpretation of assay results, only the presence or absence of ligand can be determined; semi-quantitative or quantitative determinations using these methods require that separate tests utilizing standards of known concentration be performed to establish the relationship between the observed response and the concentration of ligand.

Employing the techniques described for competitive ligand-receptor assays, the intensity of the resulting color is inversely related to the concentration of ligand in the sample such that assay results that are more intense in color than the reference are interpreted to mean that the sample contained ligand at a lower concentration than that represented by the concentration by the reference. A serious drawback, however, to the widespread utilization of such visually interpreted competitive ligand-receptor assays has been this inverse relationship between intensity of the developed signal and sample ligand concentration. This relationship provides that a sample with a low concentration of ligand will produce a large signal in the assay; and conversely a sample with a high concentration of ligand will produce a small signal in the assay. A further disadvantage of such assays is that if the requirement is for a single test to simultaneously determine multiple ligands each of which must be assigned a semi-quantitative value and each of which has specific individual concentration targets, then individual specific reference zones would have to be provided for each ligand to be determined. Under such circumstances, a test for multiple ligands becomes difficult to produce and complex to interpret.

Another prior art approach, a non-competitive immunochromatographic assay, is described in U.S. Pat. Nos. 4,168, 146 and 4,435,504. This assay provides a method for quantitatively determining the presence of a single analyte in a sample in a visually interpreted immunoassay but does not permit the assay of multiple analytes without employing multiple devices. Furthermore, in practice this method is restricted to ligands whose sample concentrations are high relative to ligands that are commonly determined by competitive assay technology. Accordingly, this type of approach is of limited utility. Clearly, there is an unmet need for a ligand-receptor assay capable of determining the presence of a multiplicity of ligands in a sample and concurrently providing individualized semiquantitative results for each ligand. Furthermore, such an assay should produce such results in a format that is simple enough for an non-technical user to correctly perform and interpret. In addition there is a need for broadly applicable quantitative assay methods that are easily performed and interpreted. The inventive methods of this invention and those described in U.S. Pat. Nos. 5,028,535 and 5,089,391 meet these requirements.

Methods to prepare monoclonal antibodies to ligands which, by themselves, do not generate an immunological response are well known to those skilled in the art. The ligand, or an analogue thereof, is generally coupled, chemically, to a carrier molecule, e.g., a protein, peptide, or other polymer, to form an immunogen (one example of a ligand analogue conjugate as defined herein) which elicits an immunological response. Antibodies are thus raised to the surface of the carrier molecule onto which is coupled the ligand. The selection or screening of antibodies is then performed to choose the antibody which best fulfills the intended use of the antibody. The screening of antibodies is well known to those skilled in the art and is generally performed by binding a ligand-carrier conjugate to a solid phase, allowing the raised antibody to bind to the ligand-carrier conjugate and detecting the presence of the bound antibody with a labelled anti-antibody conjugate. An inherent problem with the generation and screening of antibodies is the difficulty in determining the location of binding of the antibody to the ligand, i.e., the binding site; that is, it is not clear which portion of the ligand analogue is bound by the antibody. This can result in the selection of antibodies which possess a very small but definite affinity to the carrier molecule, or to the chemical structure (herein called the "linkage site") which attaches the ligand analogue to carrier molecule. Such an antibody, will thus bind (an occurrence known as crosstalk) to other, or uncomplementary, carrier molecule-ligand complexes having such a linkage, and produce false positive results when such other complexes are present in a test.

The crosstalk problem has previously been dealt with by using different linkage chemistries for attaching the ligand to the carrier molecule, and for screening the ligand-carrier conjugate; for example, see Van Weemen and Schuurs, The influence of heterologous combinations of antiserum and enzyme-labeled estrogen on the characteristics of estrogen enzyme-immunoassays, *Immunochemistry*, 12, 667 (1975). In developing ligand receptor assays for a multitude of ligands, however, creating such different chemical structures for multiple ligands can be very time consuming and expensive. In addition, this approach to developing ligand receptors is not guaranteed to be successful because the similarities of linkage chemistries, in general, make all linkage chemistries similar to a certain extent. Also, if one is attempting to prepare ligand receptors with a high degree of specificity for two molecules with very similar structures, one may be limited to the numbers of ligand analogues which can be synthesized.

The development of a ligand receptor assay capable of determining the presence of a multiplicity of ligands requires that the ligand receptors not have a substantial affinity for uncomplementary ligand analogue conjugates. A substantial affinity of a ligand receptor for an uncomplementary ligand analogue conjugate in a multi-analyte assay results in false positive results and renders the assay useless.

The present invention is related to reagents, and method of their use, which reduce or prevent the crosstalk or the undesirable interactions between ligand receptors and uncomplementary ligand analogue conjugates. The reagents, or crosstalk inhibitors, described herein mimic the chemical structure which links the ligand or ligand analogue to the carrier molecule. The extent to which the crosstalk inhibitor must or must not resemble the chemical structure of the ligand analogue linkage chemistry depends on the affinity that the ligand receptor possesses for the linkage chemistry. Thus, the reagents described herein allow the simultaneous determination of the presence of a multiplicity of ligands in a sample by inhibiting or reducing the low affinity interactions of the ligand receptors for the uncomplementary ligand-carrier molecule conjugate or other uncomplementary ligand analogue conjugates.

SUMMARY OF THE INVENTION

The present invention is directed to ligand receptor assays in which the presence of a multiplicity of ligands are measured in a single determination. In particular, the present invention relates to the preparation and use of reagents as crosstalk inhibitors in ligand receptor assays. The crosstalk inhibitors resemble the chemical structure (or linkage site) which links the ligand analogue to the carrier molecule of a ligand analogue conjugate. Thus, the crosstalk inhibitors reduce or prevent the crosstalk, i.e., the undesirable interactions between ligand receptors and uncomplementary ligand analogue conjugates.

More particularly, this invention relates to methods and reagents for the simultaneous determination of more than one target ligand in a single test format. The inventive assays described herein involve the use of crosstalk inhibitors in simultaneous multi-ligand assays. The crosstalk inhibitors resemble the chemical structure which links a ligand, or an analogue thereof, to, e.g., a signal development element of a ligand analogue conjugate, and thereby reduce or prevent undesirable interactions between ligand receptors and uncomplementary ligand analogue conjugates.

The crosstalk inhibitor is normally contained in the reaction mixture. It does not compete significantly with the complementary ligand analogue conjugate for ligand receptor binding sites in the reaction mixture. Once the binding events in the reaction mixture reflect the amounts of target ligands in the sample (also expressed as the reaction mixture reaching substantial equilibrium binding), the reaction mixture may be contacted with a terminal solid phase onto which is immobilized ligand receptor. In the absence of crosstalk inhibitor, the concentration of ligand receptor on the solid phase is such that the unbound ligand analogue conjugate can bind monovalently or multivalently to the solid phase ligand receptor or receptors. This ability of the ligand analogue conjugate to bind multivalently to the solid phase ligand receptor amplifies low affinity interactions because the effective affinity is the product of the individual affinities of the monovalent interactions. The result is that ligand receptors on the solid phase, which have low affinities for the linkage chemistries of the ligand analogue conjugates, can bind multivalently to uncomplementary ligand analogue conjugates. The product of such multivalent binding is large enough to detect a binding of uncomplementary ligand analogue conjugate to the solid phase ligand receptor as a result of the assay. Such detection provides a false positive result.

The crosstalk inhibitor, which resembles the linkage chemistry of the ligand analogue conjugates, competes with the linkage chemistry of the ligand analogue conjugates for binding to the terminal solid phase ligand receptor. With the proper crosstalk inhibitor and crosstalk inhibitor concentration, the competition is shifted toward binding of the crosstalk inhibitor and not of the uncomplementary ligand analogue conjugates. The crosstalk inhibitor should compete very poorly with the complementary ligand analogue conjugate for the solid phase ligand receptor because the affinity of the ligand receptor for the complementary ligand analogue conjugate is much higher.

How closely the chemical structure of the crosstalk inhibitor must resemble the linkage chemistry of the ligand analogue depends on the affinity of the ligand receptor for the uncomplementary ligand analogue conjugate. The crosstalk inhibitor may be free in solution or bound to a protein or polymer. When the crosstalk inhibitor is attached to a protein or polymer, it can bind multivalently to the solid phase ligand receptor as can the ligand analogue conjugate. Thus, the multivalent crosstalk inhibitor can better compete with the uncomplementary ligand analogue conjugate than the monovalent crosstalk inhibitor.

Definitions

In interpreting the claims and specification, the following terms shall have the meanings set forth below.

Complementary Ligand Analogue Conjugate—This ligand analogue conjugate binds to its intended ligand receptor at the binding site. By intended ligand receptor is meant, e.g., a ligand receptor produced by standard immunological techniques to the conjugate itself, or to its equivalent analogue. Those of ordinary skill in the art will recognize the scope of this term when used to describe non-antibody ligands, and their conjugates. As an example, in the antibody-type ligand area, a complementary ligand analogue conjugate will have a higher affinity for its intended ligand receptor of at least $10^5$ $M^{-1}$ (for monovalent binding), and preferably higher, and an uncomplementary ligand analogue conjugate (see below) will have a lower affinity (for monovalent binding) for this ligand receptor than the complementary ligand analogue conjugate.

Complementary Ligand Receptor—This ligand receptor binds its intended ligand analogue conjugate at the binding site.

Crosstalk—The binding of the uncomplementary ligand conjugate to the ligand receptor, e.g., at the linkage site of the conjugate. Also, the binding of an uncomplementary ligand receptor conjugate to a ligand analogue.

Crosstalk inhibitor—The crosstalk inhibitor is an analogue or analogues of the linkage chemistry, at a linkage site, which is used to attach ligand analogue to a protein, polypeptide, polymer or molecular complex, and reduces or prevents the binding of an uncomplementary ligand analogue conjugate to ligand receptor or the uncomplementary ligand receptor conjugate to ligand analogue. It does not interfere significantly with binding of a complementary ligand analogue conjugate at its binding site to a ligand receptor. The crosstalk inhibitor can be free in solution, alone or bound to itself as a dimer or multimer, or it can be attached to proteins, polypeptides, polymers or molecular complexes.

Ligand—Binding partner to ligand receptor.

Ligand Analogue—A chemical derivative of the ligand which may be attached either covalently or noncovalently to other species, for example, to the signal development element. Ligand analogue and ligand may be the same, and both are capable of binding to ligand receptor.

Ligand Analogue Conjugate—A conjugate of a ligand analogue and a signal development element, a protein, polypeptide, or polymer. When a non-signal development element (the ligand analogue conjugate of which is herein termed a ligand analogue construct) is used, its presence in an assay as a binding partner may be detected by standard procedure, e.g., using methodology commonly used in sandwich assays, such as a labelled antibody to the ligand analogue construct.

Ligand Receptor—Receptor capable of binding ligand, typically an antibody, but which may be another ligand, depending on assay design.

Binding domain—shall refer to the molecular structure associated with that portion of a receptor that binds ligand. More particularly, the binding domain may refer to a polypeptide, natural or synthetic, or nucleic acid encoding such a polypeptide, whose amino acid sequence represents a specific region of a protein, said domain, either alone or in combination with other domains, exhibiting binding characteristics which are the same or similar to those of a desired ligand/receptor binding pair. Neither the specific sequences nor the specific boundries of such domains are critical, so long as binding activity is exhibited. Likewise, used in this context, binding characteristics necessasrily includes a range of affinities, avidities and specificities, and combinations thereof, so long as binding activity is exhibited.

Linking group—shall mean the "chemical arm" between the protein, polypeptide or label and a drug or drug derivative. As one skilled in the art will recognize, to accomplish the requisite chemical structure, each of the reactants must contain the necessary reactive groups. Representative combinations of such groups are amino with carboxyl to form amide linkages, or carboxy with hydroxy to form ester linkages or amino with alkyl halides to form alkylamino linkages, or thiols with thiols to form disulfides, or thiols with maleimides or alkkylhalides to form thioethers. Obviously, hydroxyl, carboxyl, amino and other functionalities, where not present may be introduced by known methods. Likewise, as those skilled in the art will recognize, a wide variety of linking groups may be employed. The structure of the linkage should be a stable covalent linkage formed to bind the drug or drug derivative to the protein, polypeptide or label. In some cases the linking group may be designed to be either hydrophilic or hydrophobic in order to enhance the desired binding characteristics of the ligand and the receptor. The covalent linkages should be stable relative to the solution conditions under which the ligand and linking group are subjected. Generally preferred linking groups will be from 1–20 carbons and 0–10 heterocarbons (NH, O, S) and may be branched or straight chain. Without limiting the foregoing, it should be obvious to one skilled in the art that only combinations of atoms which are chemically compatible comprise the linking group. For example, amide, ester, thioether, thioester, keto, hydroxyl, carboxyl, ether groups in combinations with carbon-carbon bonds are acceptable examples of chemically compatible linking groups. Other chemically compatible compounds which may comprise the linking group are set forth in this Definition section and hereby are incorporated by reference.

Hydrocarbyl—shall refer to an organic radical comprised of carbon chains to which hydrogen and other elements are attached. The term includes alkyl, alkenyl, alkynyl and aryl groups, groups which have a mixture of saturated and unsaturated bonds, carbocyclic rings and includes combinations of such groups. It may refer to straight-chain, branched-chain cyclic structures or combinations thereof.

aryl—shall refer to aromatic groups which have at least one ring having a conjugated pi electron system and includes carbocyclic aryl, heterocyclic aryl and biaryl groups, all of which may be optionally substituted.

Carbocyclic aryl groups—shall refer to groups wherein the ring atoms on the aromatic ring are carbon atoms. Carbocyclic aryl groups include monocyclic carbocyclic aryl groups and optionally substituted naphthyl groups.

Monocyclic carbocyclic aryl—shall refer to optionally substituted phenyl, being preferably phenyl or phenyl substituted by one to three substituents, such being advantageously lower alkyl, hydroxy, lower alkoxy, lower alkanoyloxy, halogen, cyano, trihalomethyl, lower acylamino, lower amino or lower alkoxycarbonyl.

Optionally substituted naphthyl—shall refer to 1- or 2-naphthyl or 1- or 2-naphthyl preferably substituted by lower alkyl, lower alkoxy or halogen.

Heterocyclic aryl groups—shall refer to groups having from 1 to 3 heteroatoms as ring atoms in the aromatic ring and the remainder of the ring atoms carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl, and the like, all optionally substituted.

Optionally substituted furanyl—shall refer to 2- or 3-furanyl or 2- or 3-furanyl preferably substituted by lower alkyl or halogen.

Optionally substituted pyridyl—shall refer to 2-, 3- or 4-pyridyl or 2-, 3- or 4-pyridyl preferably substituted by lower alkyl or halogen.

Optionally substituted thienyl—shall refer to 2- or 3-thienyl, or 2- or 3-thienyl preferably substituted by lower alkyl or halogen.

biaryl—shall refer to phenyl substituted by carbocyclic aryl or heterocyclic aryl as defined herein, ortho, meta or para to the point of attachment of the phenyl ring, advantageously para; biaryl is also represented as the —$C_6H_4$—Ar substituent where Ar is aryl.

aralkyl—shall refer to an alkyl group substituted with an aryl group. Suitable aralkyl groups include benzyl, picolyl, and the like, and may be optionally substituted.

lower—referred to herein in connection with organic radicals or compounds respectively defines such with up to and including 7, preferably up to and including 4 and advantageously one or two carbon atoms. Such groups may be straight chain or branched.

The terms (a) "alkyl amino", (b) "arylamino", and (c) "aralkylamino", respectively, shall refer to the groups —NRR' wherein respectively, (a) R is alkyl and R' is hydrogen or alkyl; (b) R is aryl and R' is hydrogen or aryl, and (c) R is aralkyl and R' is hydrogen or aralkyl.

The term "acyl" shall refer to hydrocarbyl-CO— or HCO—.

The terms "acylamino" refers to RCONCR)— and ($RCO_2N$— respectively, wherein each R is independently hydrogen or hydrocarbyl.

The term "hydrocarbyloxycarbonyloxy" shall refer to the group ROC(O)O— wherein R is hydrocarbyl.

The term "lower carboalkoxymethyl" or "lower hydrocarbyloxycarbonmethyl" refers to hydrocarbyl-OC(O)$CH_2$— with the hydrocarbyl group containing ten or less carbon atoms.

The term "carbonyl" refers to —C(O)—. The term "carboxamide" or "carboxamido" refers to —$CONR_2$ wherein each R is independently hydrogen or hydrocarbyl.

The term "lower hydrocarbyl" refers to any hydrocarbyl group of ten or less carbon atoms.

The term "alkyl" refers to saturated aliphatic groups including straight-chain, branched chain and cyclic groups.

The term "alkenyl" refers to unsaturated hydrocarbyl groups which contain at least one carbon-carbon double bond and includes straight-chain, branched-chain and cyclic groups.

The term "alkynyl" refers to unsaturated hydrocarbyl groups which contain at least one carbon-carbon triple bond and includes straight-chain, branched-chain and cyclic groups.

The term "hydrocarbyloxycarbonylamino" refers to a urethane, hydrocarbyl-O—CONR— wherein R is H or hydrocarbyl and wherein each hydrocarbyl is independently selected. The term "di(hydrocarbyloxycarbonyl)amino" refers to (hydrocarbyl-O—CO)$_2$N— wherein each hydrocarbyl is independently selected.

The term "hydrocarbylamino" refers to —NRR' wherein R is hydrocarbyl and R' is independently selected hydrocarbyl or hydrogen.

The term "mercapto" refers to SH or a tautomeric form.
The term "methine" refers to

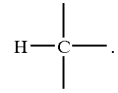

The term "methylene" refers to —$CH_2$—,
The term "alkylene" refers to a divalent straight chain or branched chain saturated aliphatic radical.
The term "oxy" refers to —O— (oxygen).
The term "thio" refers to —S— (sulfur).
Disulfide—refers to —S—S—.
Thioether—refers to C—S—C.
Ester—refers to

Reaction Mixture—In a competitive immunoassay, the mixture of sample suspected of containing the target ligand and the assay reagents that participate in the competitive binding reactions.

Signal Development Element—The element of the ligand analogue conjugate, e.g., an enzyme, which, in conjunction with the signal development phase, develops a detectable signal. Signal Development Phase—The phase containing the materials enabling the signal development element to develop signal, e.g., an enzyme substrate solution.

Signal Development System—A system which includes those reagents necessary to detect binding of a binding pair.

Terminal Solid Phase—The solid phase upon which the signal is finally developed during signal development.

Threshold Concentration—The concentration of ligand in a sample which results in the first detectable signal development. A threshold concentration is a concentration reference point.

Uncomplementary Ligand Analogue Conjugate—This ligand analogue conjugate binds to ligand receptors other than its intended ligand receptor, at its linkage site or another site, but not at its binding site.

Uncomplementary Ligand Receptor—This ligand receptor binds an unintended ligand analogue conjugate at the linkage site. (A particular ligand receptor may be both a complementary and an uncomplementary ligand receptor dependent upon the ligand analogue conjugate in issue.)

Thus, in a first aspect, the invention features an assay for detecting the amount or presence of target ligand in a sample. The assay includes a ligand analogue conjugate having a linkage site and a binding site, a ligand receptor, and a sample. The assay includes the steps of providing at least one crosstalk inhibitor. This inhibitor, under assay conditions, competes with the linkage site of the ligand analogue conjugate for binding to the ligand receptor, and does not compete with the binding site of the ligand analogue conjugate for binding to the ligand receptor. In the invention, the assay is performed for the target ligand in the presence of a sufficient amount of the crosstalk inhibitor to reduce the amount of binding of the linkage site of the uncomplementary ligand analogue conjugate to the ligand receptor.

By "not compete" is meant that while the crosstalk inhibitor may compete to some extent with binding of the binding site of the ligand analogue conjugate and the ligand receptor, that competition does not prevent detection of a positive interaction between the ligand analogue conjugate and ligand receptor. That is, the amount of competition is not significant in the assay, since the assay still provides a detectable true positive result, with fewer false positive results. It is important in this invention that such a true positive interaction is still observable, and that the number or amount of false positive results is reduced. Examples of such non-competition are provided below in the examples. Those of ordinary skill in this art will recognize that these examples show and elaborate on the meaning of the term "not compete". Thus, while a positive response may be reduced by 50% or more, it is important only that this result is detectable, and that the false positive response is reduced to a low level, preferably to an undetectable level. A crosstalk inhibitor which produces such a result is useful in this invention and is said to "not compete" with the binding site of the ligand analogue conjugate for the ligand receptor, but to "compete" with the linkage site of the ligand analogue conjugate for the ligand receptor.

In a related aspect, the invention features an assay for detecting the amount or presence of a plurality of target ligands in a sample. This assay includes a plurality of ligand analogue conjugates corresponding to the plurality of target ligands. Each ligand analogue conjugate has a linkage site and a binding site; the binding site of each ligand analogue conjugate is generally different from the binding site of other ligand analogues conjugates. The linkage site of each ligand analogue conjugate may be the same or different. The assay also includes a plurality of ligand receptors. Each ligand receptor binds with only one target ligand of the plurality of target ligands, and not with the other target ligand, with each ligand receptor binding with a different target ligand. The assay also includes a sample. In the method, at least one crosstalk inhibitor is provided. This crosstalk inhibitor, under assay conditions, competes with the linkage site of at least one ligand analogue conjugate for binding to at least one ligand receptor, and does not compete with any of the binding sites of the plurality of ligand analogue conjugates for binding to the plurality of ligand receptors. Finally, in the method, an assay is performed for the target ligands in the presence of a sufficient amount of the crosstalk inhibitor to reduce the amount of binding to the linkage site of at least one ligand analogue conjugate to at least one uncomplementary ligand receptor.

In another aspect, the invention features a method for identifying a crosstalk inhibitor useful in an assay which detects the presence or amount of target ligand in a sample. The assay includes a complementary ligand analogue conjugate having a linkage site and a binding site, a ligand receptor and a sample. In the method, a potential crosstalk inhibitor is provided and a test performed which includes essentially the following components: the ligand analogue conjugate, an uncomplementary ligand receptor, and a signal development system. In this test, a positive result is attained in the absence of a crosstalk inhibitor (i.e., a false positive result is attained). This test is also performed in the presence of the potential crosstalk inhibitor. A reduced false positive result in the presence of crosstalk inhibitor as compared to the false positive result obtained in the absence of the crosstalk inhibitor indicates that the potential crosstalk inhibitor is a useful crosstalk inhibitor. Such a reduced false positive result is generally a result of competition between the crosstalk inhibitor and the uncomplementary ligand analogue conjugate for the ligand receptor. (The term "competition" is herein defined as the phenomenon observed to occur between crosstalk inhibitors, in the examples provided below, and the ligand analogue conjugates for the ligand receptor.)

In a preferred embodiment, the potential crosstalk inhibitor is also tested in an assay which provides a true positive result to ensure that such a true positive result is still attained in the presence of the inhibitor. The inhibitor is useful when it allows detection of such a positive result and reduces the level of false positive results. By varying the concentration of the inhibitor, or by varying its valency (e.g., by providing inhibitor bound multivalently to BSA) the use of such an inhibitor can be optimized. Examples of such variations are provided below.

In yet another aspect, the invention features a crosstalk inhibitor useful in an assay for detecting the amount or presence of an analyte in a sample. The assay includes at least one ligand analogue conjugate having a linkage site and a binding site, at least one ligand receptor and a sample. The crosstalk inhibitor competes with the linkage site of the ligand analogue conjugate for binding to the ligand receptor and does not compete with the binding site of the ligand analogue conjugate for binding to the ligand receptor.

DETAILED DESCRIPTION

The drawings will first briefly be described.

DRAWINGS

FIGS. 1A–1F shows the chemical formulae of various ligand analogue conjugates (FIGS. 1A and 1B) and the design of various useful crosstalk inhibitors (FIGS. 1C–1F); and FIGS. 2–8 are graphical representations showing the phenomenon of crosstalk, and the effect of crosstalk inhibitors on this phenomenon (CI stands for crosstalk inhibitor; w/CI stands for with crosstalk inhibitor).

FIGS. 9A–B shows the chemical formulae of the compositions of Examples 8–13, infra.

The selection and use of a crosstalk inhibitor will be explained in this section.

Selection of a Crosstalk Inhibitor

Ligand receptor assays capable of determining the presence of a multiplicity of ligands in a sample require multiple ligand receptors and complementary ligand analogue conjugates. Each ligand receptor in the reaction mixture and on the terminal solid phase has a complementary ligand analogue conjugate as its intended binding partner. The unintended binding partners for each ligand receptor are the uncomplementary ligand analogue conjugates. Generally, in a competitive assay, a reaction mixture which is comprised of the necessary ligand receptors, the complementary ligand analogue conjugates, and a sample which may contain target ligand is incubated until the binding reactions reflect the amounts of ligands in the sample, preferably to equilibrium. The reaction mixture may then be contacted with a terminal solid phase which has immobilized, in discrete zones, ligand receptors to the complementary ligand analogue conjugates. These solid phase ligand receptors bind ligand analogue conjugates not bound by ligand receptor in the reaction mixture. The detectable responses from such binding are related to the presence or amount of target ligand. Because of the inherent low affinity for the linkage chemistry of the ligand analogue conjugate that a ligand receptor may possess, (see Background of the Invention) the solid phase ligand receptor may bind to uncomplementary ligand analogue conjugates. This indiscriminate binding will result in false positive results in the assay at discrete zones on the solid phase containing ligand receptors which interact with ligand analogue conjugates with such linkage site chemistry. However, the crosstalk inhibitor which is contained in the reaction mixture will compete with the linkage site chemistry of the ligand analogue conjugate for binding to the solid phase ligand receptor. Thus, the design of the crosstalk inhibitor depends on the relative affinities which the ligand receptor possesses for the ligand analogue of the ligand analogue conjugate (the binding site) and for the linkage site chemistry of the ligand analogue conjugate (the linkage site). The higher the affinity for the linkage site chemistry relative to the ligand analogue of the ligand analogue conjugate the more the crosstalk inhibitor must resemble the linkage site chemistry. In practice (see examples below), several analogues of the linkage site chemistry are synthesized with differing resemblances to the linkage site chemistry. Each of the crosstalk inhibitors at an appropriate concentration are added to the reaction mixture and the binding reaction is allowed to come, preferably, to substantial equilibrium. The reaction mixture is then added to a terminal solid phase comprising the respective ligand receptors in discrete zones. After a wash step which removes the unbound ligand analogue conjugate, the effective crosstalk inhibitor prevents or reduces the binding of the uncomplementary ligand analogue conjugate to the solid phase ligand receptor.

For example, consider the following model for the linkage site chemistry which attaches the ligand to form the ligand analogue conjugate:

where A,B,C and D represent similar and/or different atoms or groups of atoms, L represents the ligand or ligand analogue, P represents the structure onto which the linkage site chemistry attaches the ligand and the "-" represents a chemical bond. Taken together, A-B-C-D defines the linkage chemistry, which collectively may be termed "Z." Z is an aliphatic or aromatic linking group of from 1–50 carbons and 0–20 heterocarbons (NH, O, S) and may be branched or straight chain. Potential effective crosstalk inhibitors (which may sometimes herein be referred to as Z') would be comprised of, but not limited to: A, A-B, A-B-C, A-B-C-D, A-P, A-B-P, A-B-C-P and A-B-C-D-P. Other potential effective crosstalk inhibitors would include those stated above with portions of the ligand molecule also attached, and/or the portions of the linkage site chemistry attached to structures other than P, such as, different proteins or polymers. Crosstalk inhibitors are those compounds which are capable of competing with at least a portion of Z for binding to a desired receptor. The crosstalk inhibitor structure is not limited to only the atoms comprising the linkage site chemistry because it is well known to those skilled in the art that atoms with similar stereochemistries and sizes could substitute for the actual linking atoms; e.g., a ligand receptor may not always distinguish a carboxylic ester from an amide group, and thus an ester in the linkage chemistry of the ligand analogue conjugate may be substituted for an amide in the inhibitor. Thus, an effective crosstalk inhibitor may be defined as a molecule which minimizes or prevents the binding of an uncomplementary ligand analogue conjugate or like molecule to the terminal solid phase ligand receptor, without significantly affecting binding of the ligand to the desired binding site.

In the reaction mixture, the crosstalk inhibitor should not compete (as defined above) with either the binding site of the ligand analogue conjugate or the target ligand for binding to the ligand receptor. The competition of the crosstalk inhibitor with the ligand analogue conjugate in the reaction mixture would manifest itself by shifting the dose response curve of the competitive immunoassay for the target ligand or by changing the threshold concentration in assays as described in U.S. Pat. Nos. 5,028,535 and 5,089,391, incorporated herein by reference. This competition in the reaction mixture can be affected by several factors: 1) The more the crosstalk inhibitor resembles the linkage site chemistry of the ligand analogue conjugate, the greater is the possibility that the crosstalk inhibitor will significantly compete with the ligand analogue conjugate for ligand receptor. It may also compete with the target ligand for ligand receptor if the crosstalk inhibitor resembles too closely the target ligand. Such competition is not due to any similarity in structure of the ligand and the inhibitor, but due to their joint recognition by the same ligand receptor. This phenomenon will normally only occur at high inhibitor concentration, or high valency, since the ligand has a higher affinity for the ligand receptor than does the inhibitor. 2) If the crosstalk inhibitor is monovalent or unattached in the reaction mixture it can only bind monovalently to the ligand receptor. This condition minimizes the competition because monovalent interactions, as compared to multivalent interactions, are the weakest.

Furthermore, the ligand analogue conjugate generally is comprised of multiple ligands (that is, the same or different multiple ligands) so that the ligand receptor may bind bivalently to the complementary ligand analogue conjugate. Thus, the bivalent binding of the ligand receptor to the complementary ligand analogue conjugate is greatly favored over the monovalent binding of the free crosstalk inhibitor to the ligand analogue conjugate. This condition may not be desirable in practice because the outcome would be that the target ligand may not sufficiently compete with ligand analogue conjugate for binding ligand receptor. 3) If the crosstalk inhibitor is multiply attached to a protein or polymer, the ligand receptor may bind bivalently to the crosstalk inhibitor. This condition gives the greatest possibility for the crosstalk inhibitor to compete with the linkage site of the ligand analogue conjugate for binding to the ligand receptor. However, the competition can be minimized by using a labelling density of the crosstalk inhibitor on the protein or polymer which does not allow the ligand receptor to span the surface of the structure and bind bivalently. In this context, the size of the protein or polymer is important. For example, if the protein or polymer diameter is substantially smaller than the distance between the binding arms of the antibody, then the antibody cannot bind bivalently to the crosstalk inhibitor, regardless of the labelling density of the crosstalk inhibitor. 4) If the ligand receptor can only bind monovalently to the ligand analogue conjugate or the crosstalk inhibitor, (for example, if the ligand receptor is a Fab fragment of an antibody) then the probability of competition is simply a function of the relative affinities and concentrations of the ligand analogue conjugate and the crosstalk inhibitor for the ligand receptor.

Once the reaction mixture comes to substantial equilibrium without the crosstalk inhibitor substantially affecting the binding of the ligand receptors to their respective binding site of the complementary ligand analogue conjugates or the target ligands, the reaction mixture is contacted with a terminal solid phase onto which ligand receptors are immobilized in discrete zones. The ligand receptors are specific for their complementary binding sites on ligand analogue conjugates. The ligand receptors may also have an affinity for the linkage site chemistry of the ligand analogue conjugate. The effective crosstalk inhibitor will compete with the linkage site chemistry of the ligand analogue conjugate, thus preventing the binding of uncomplementary linkage sites of ligand analogue conjugates to the terminal solid phase ligand receptors. In the absence of crosstalk inhibitor in the reaction mixture, the binding of uncomplementary ligand analogue conjugate to the terminal solid phase ligand receptors can be detected as false positive responses after a wash step to remove unbound ligand analogue conjugate. In the presence of the effective crosstalk inhibitor in the reaction mixture, the binding of uncomplementary ligand analogue conjugate is not detected after the wash step. Thus, with the proper crosstalk inhibitor and crosstalk inhibitor concentration, the competition of the linkage site chemistry of the ligand analogue and the crosstalk inhibitor for binding to the terminal solid phase ligand receptor is shifted toward binding of the crosstalk inhibitor. The crosstalk inhibitor should compete very poorly with the complementary binding site of the ligand analogue conjugate for the terminal solid phase receptor because the affinity of the ligand receptor for the complementary binding site of the ligand analogue conjugate is much higher. If the crosstalk inhibitor substantially competes with the complementary binding site of the ligand analogue conjugate for binding to the terminal solid phase receptor, then the signal on the terminal solid phase will be depressed relative to the condition where the crosstalk inhibitor is absent from the reaction mixture. In this latter case, the crosstalk inhibitor substantially changes the binding of the ligand analogue conjugate to the terminal solid phase ligand receptor. This problem can be minimized, prevented, or caused by the following conditions: 1) The crosstalk inhibitor may resemble, too closely, the linkage site chemistry. This may be particularly true if the crosstalk inhibitor is monovalent and unattached to a protein or polymer. Crosstalk inhibitors should be synthesized which have less resemblance to the linkage chemistry. 2) If the crosstalk inhibitor is attached to a protein or polymer, the degree of derivitization or the concentration of the crosstalk inhibitor may be too high. The degree of derivitization and/or the concentration of the crosstalk inhibitor should be decreased in the reaction mixture. As the degree of derivitization of the crosstalk inhibitor increases, the affinity of the crosstalk inhibitor for the terminal solid phase ligand receptor increases. This is because the crosstalk inhibitor can bind multivalently to the terminal solid phase ligand receptors which are immobilized at a very high local concentration. The resulting affinity of the crosstalk inhibitor for the ligand receptor allows the crosstalk inhibitor to compete with the linkage site of the ligand analogue conjugate. Thus, the effective crosstalk inhibitor should compete equally or better than the linkage site of the uncomplementary ligand analogue conjugate and very poorly or insignificantly with the complementary binding site of the ligand analogue conjugate for the terminal solid phase ligand receptor. 3) The mass of antibody on the terminal solid phase may be too low which results in the crosstalk inhibitor depressing the specific signal. This occurs because the crosstalk inhibitor competes with the linkage site of the ligand analogue conjugate for binding with the solid phase antibody and when the solid phase antibody is limiting less ligand analogue conjugate will bind. This problem can be circumvented by increasing the mass of antibody on the solid phase so that it is in substantial excess over the concentration of ligand analogue conjugate.

Ligand Receptor Assay Processes Using Crosstalk Inhibitor

In some heterogeneous, competitive assay processes of the present invention, the reaction mixture is formed by contacting the sample, ligand analogue conjugates, crosstalk inhibitor, and ligand receptors that are immobilized in discrete zones on a solid phase, each zone being specific for a target ligand. The reaction mixture is allowed to incubate until the amounts of ligand analogue conjugates bound to the ligand receptor zones are related to the concentrations of the target ligands in the sample. Alternatively, the sample is contacted with the solid phase followed by contact of the ligand analogue conjugates and crosstalk inhibitor with the solid phase. The unbound ligand analogue conjugates may be washed away from the solid phase before contact with a signal development phase or methods such as those described in U.S. Pat. Nos. 4,233,402 and 4,391,904 may be employed to develop the signal without washing. The signal developed at each discrete zone of immobilized ligand receptor is related to the concentration of its respective target ligand by calibration methods well-known to those skilled in the art. It is important to note that the discrete zones of immobilized ligand receptors must be separated in space by a sufficient distance so that binding of ligand analogue conjugate to one zone does not deplete the concentration of ligand analogue conjugate available for competitive reactions in a neighboring zone. Solid phases where the ligand receptor zones are immobilized on a surface such as a porous membrane are preferred for this reason.

In other heterogeneous, competitive assay processes of the present invention the reaction mixture is formed by contacting the sample, crosstalk inhibitor, soluble ligand receptors for each target ligand, and ligand analogue conjugates. The reaction mixture is allowed to incubate until the amounts of ligand analogue conjugates bound to the ligand receptors are related to the amounts of the target ligands in the sample. The reaction mixture is then contacted with a solid phase comprising discrete zones of immobilized ligand receptors, each zone being specific for a target ligand. The ligand analogue conjugates that are not bound by ligand receptors are able to bind to their respective zones on the solid phase. The unbound ligand analogue conjugates may be washed away from the solid phase before contact with a signal development phase or methods such as those described in U.S. Pat. Nos. 4,233,402 and 4,391,904 may be employed to develop the signal without washing. The signal developed at each discrete zone of immobilized ligand receptor is related to the concentration of its respective target ligand by calibration methods well-known to those skilled in the art. Preferred assay methods employ a terminal solid phase which contains receptors immobilized in discrete zones on a porous member, each zone being specific for one of the target ligands. Particularly preferred assay methods employ terminal solid phases with discrete zones containing immobilized ligand analogue antibodies such as those described in co-pending U.S. patent application Ser. No. 583,046 filed Sep. 14, 1990, assigned to the same assignee as the present invention, and hereby incorporated by reference herein.

In some heterogeneous, competitive assay processes of the present invention, the reaction mixture is formed by contacting the sample, crosstalk inhibitor, and ligand receptor conjugates comprising at least one ligand receptor capable of binding target ligand, and ligand analogues that are immobilized in discrete zones on a solid phase, each zone being specific for a target ligand. The reaction mixture is allowed to incubate until the amounts of ligand receptor conjugate bound to the ligand analogue zones are related to the concentrations of the target ligands in the sample. Alternatively, the sample is contacted with the solid phase followed by contact of the conjugate and the crosstalk inhibitor with the solid phase. The unbound ligand receptor conjugate may be washed away from the solid phase before contact with a signal development phase or methods such as those described in U.S. Pat. Nos. 4,233,402 and 4,391,904 may be employed to develop the signal without washing. As above, the signal developed at each discrete zone of immobilized ligand analogues is related to the concentration of its respective target ligand by calibration methods well-known to those skilled in the art.

In other heterogeneous, competitive assay processes of the present invention the reaction mixture is formed by contacting the sample, ligand analogue constructs for each target ligand, crosstalk inhibitor and ligand receptor conjugate coupled to a signal development element, each ligand receptor conjugate comprising at least one ligand receptor capable of binding target ligand. The reaction mixture is allowed to incubate until the amounts of ligand receptor conjugate not bound to the ligand analogue constructs are related to the amounts of the target ligands in the sample. The reaction mixture is then contacted with a solid phase comprising discrete zones of immobilized ligand analogues, each zone being specific for a target ligand. The ligand receptor conjugates that are not bound by ligand analogue constructs are able to bind to their respective zones on the solid phase. The unbound ligand receptor conjugate may be washed away from the solid phase before contact with a signal development phase or methods such as those described in U.S. Pat. Nos. 4,233,402 and 4,391,904 may be employed to develop the signal without washing. As above, the signal developed at each discrete zone of immobilized ligand analogues is related to the concentration of its respective target ligand by calibration methods well-known to those skilled in the art. Preferred assay methods employ a terminal solid phase which contains ligand analogues immobilized in discrete zones on a porous member, each zone being specific for one of the target ligands.

In the context of these formats, the crosstalk inhibitor: 1) reduces or prevents the binding of uncomplementary ligand analogue conjugate to the solid phase ligand receptor by competing with the linkage chemistry of the ligand analogue conjugate for binding to the solid phase ligand receptor, 2) reduces or prevents the binding of uncomplementary ligand receptor conjugate to solid phase ligand analogue by competing with the linkage chemistry of the solid phase ligand analogue, and 3) reduces or prevents the binding of uncomplementary ligand receptor conjugate to both the ligand analogue construct and the solid phase ligand analogues by competing with the linkage chemistry of both the ligand analogue construct and the solid phase ligand analogue.

In ligand receptor assays utilizing a solid phase ligand receptor to capture unbound ligand analogue conjugate, a common problem incurred is that when samples contain a very high concentration of target ligand, the target ligand and the ligand analogue conjugate compete for binding sites on the solid phase ligand receptor. The result of this competition is that the ligand analogue conjugate may not bind to the solid phase ligand receptor and the interpretation of the assay may be a negative result. This problem of judging samples negative when large amounts of target ligand bind to the solid phase at the expense of the ligand analogue conjugate is referred as the "hook" by those skilled in the art. The problem of the hook in ligand receptor assays is the subject of two co-pending U.S. patent applications Ser. Nos. 583,046 and 583,556, both filed Sep. 14, 1990, assigned to the same assignee as the present invention, and both herein incorporated by reference. One of these co-pending patent applications (Ser. No. 583,046, filed Sep. 14, 1990) teaches that the solid phase ligand receptor should have a higher affinity for the ligand analogue conjugate than the target ligand. This implies or suggests that the solid phase ligand receptor may recognize all or a portion of the linkage chemistry of the ligand analogue conjugate in addition to the ligand of the ligand analogue conjugate. The use of these "ligand analogue antibodies" is particularly preferred in ligand analogue assays to overcome the hook. Thus, in the context of using ligand analogue antibodies in ligand receptor assays, the crosstalk inhibitor will still compete with the linkage chemistry of the ligand analogue conjugate. Furthermore, since the ligand analogue antibody recognizes the ligand of the ligand analogue conjugate, as well as possibly, a portion of the linkage chemistry, the crosstalk inhibitor will compete with all or the portion of the linkage chemistry of the ligand analogue conjugate such that in the presence of the crosstalk inhibitor in a reaction mixture, the crosstalk in the ligand receptor assay will be reduced or prevented. The selection of crosstalk inhibitors for ligand analogue assays utilizing ligand analogue antibodies proceeds in a manner similar to that described for ligand receptor assays utilizing ligand receptors.

Those skilled in the art will appreciate that the means for identifying the free or unbound ligand analogue conjugate in the reaction mixture, which is related to the amount of target ligand in the sample, are numerous. Furthermore, there exists a use for crosstalk inhibitors in homogeneous assays in which free ligand analogue conjugate is not separated from bound. For example, immunoassay methods teach that the binding of a ligand analogue enzyme subunit to a ligand receptor enzyme subunit results in the activation of the enzyme in an amount proportional to the ligand concentration of the sample. In this assay format using multiple ligand analogue enzyme subunits and ligand receptor enzyme subunits, the crosstalk inhibitor can reduce or prevent the ligand receptor from binding to its uncomplementary ligand analogue enzyme subunit. Also, immunoassay methods teach that a change in fluorescence polarization of a fluorescent ligand attached to a ligand receptor occurs when a ligand analogue conjugate competes with ligand. The change in florescence polarization reflects the ligand concentration in the sample. In this assay format when multiple fluorescent ligand conjugates and ligand receptors are used, the crosstalk inhibitor can reduce or prevent the binding of ligand receptor to the uncomplementary fluorescent ligand conjugates. In addition, U.S. Pat. No. 3,817,837 teach that an antibody binding to a ligand analogue enzyme conjugate as a result of the assay process causes an inactivation of the enzyme. The extent of enzyme inactivation is then correlated to ligand concentration. In this assay format, when multiple ligand analogue enzymes, ligand analogues and enzyme substrates are used to perform an immunoassay on multiple ligands in a single determination, the crosstalk inhibitor may be used to reduce or prevent the binding of uncomplementary ligand analogue enzyme conjugate to ligand receptor. Thus, this invention teaches that crosstalk inhibitors can be used when multiple binding interactions, occurring in a solution or on a solid phase, result in the binding of ligand receptor to an uncomplementary ligand analogue conjugate or conversely, when the multiple binding interactions result in the binding of uncomplementary ligand receptor conjugate to ligand analogue.

Figure 1C:
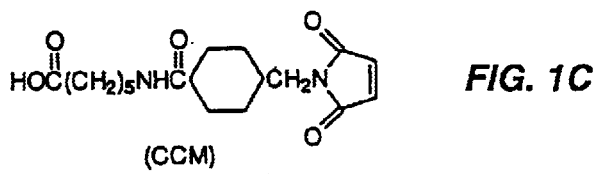
Figure 1D:
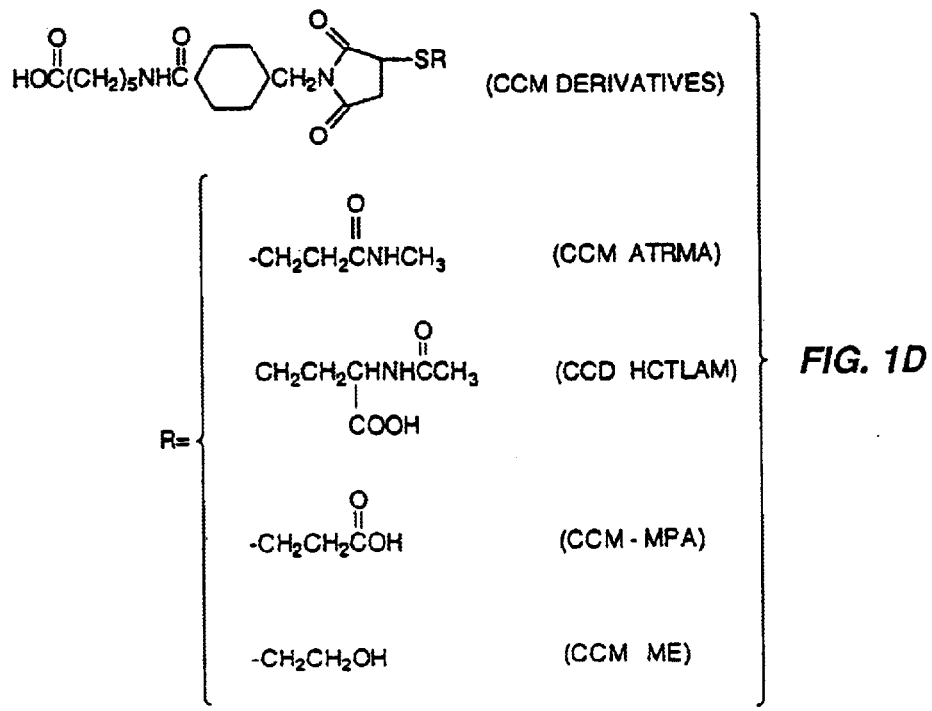
Figure 1E:
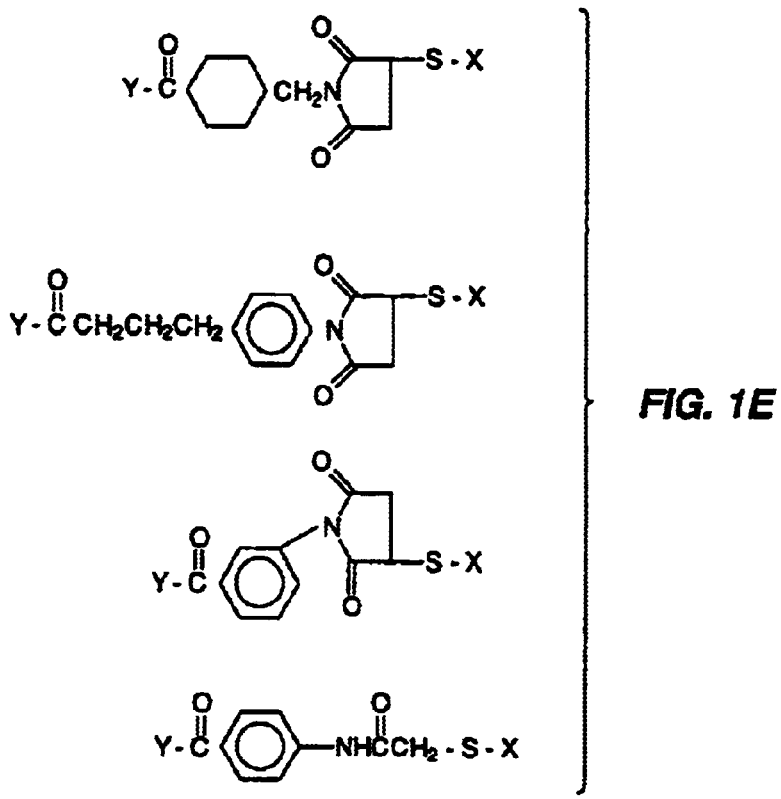
Figure 1F:
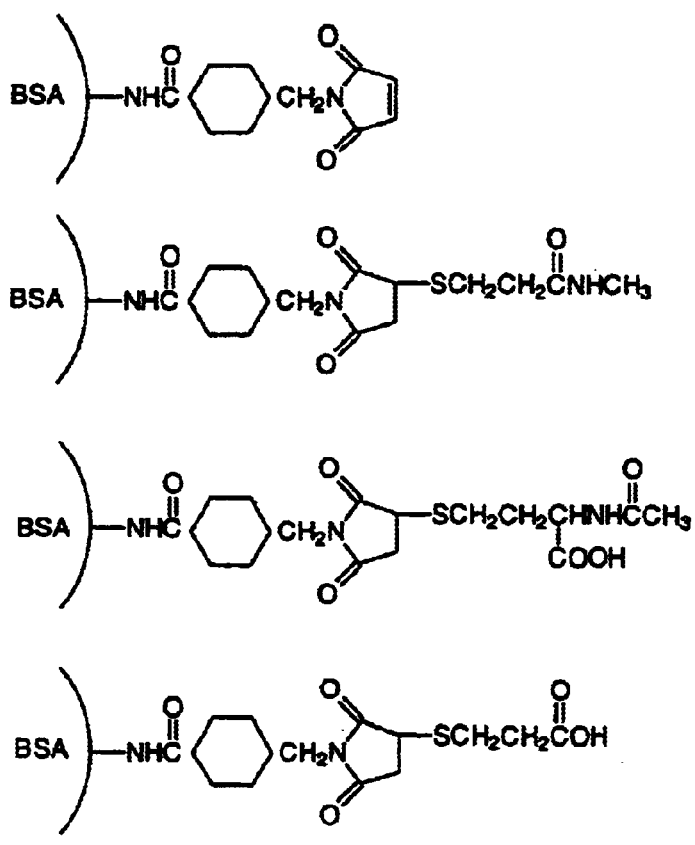

There follows various examples which illustrate to those of ordinary skill in the art the methodology and processes by which crosstalk inhibitors of the invention can be designed. In addition, examples of the chemical synthesis of various described chemicals are provided. Thus, referring to FIGS. 1A–1F, there are shown two examples of the chemical linkage between BSA and amphetamine or morphine (FIG. 1A and FIG. 1B, respectively), and examples of crosstalk inhibitors which will compete for binding by antibodies to the linkage chemistries of the amphetamine and morphine analogue conjugates (FIGS. 1C, 1D, and 1F). By way of example and not by limitation, those of ordinary skill in the art will recognize that FIG. 1E is illustrative of the general formulae of some crosstalk inhibitors. In FIG. 1E, Y represents a protein, polymer or polypeptide or its equivalent, for example, BSA, generally having an amide bond, or Y may simply be a bond or an alkyl chain containing 1–10 carbon atoms with up to five heteroatoms. X may also be a bond or an alkyl chain containing 1–10 carbon atoms with up to five heteroatoms, or may be an alkyl chain of 1–5 alkyl groups containing one or more ketone or carboxyl acid groups and one or more amide or alcohol groups. Examples of the chemical formula for X are identical to those shown for R in FIG. 1D. In general, the chemical linkage group shown in FIGS. 1A and 1B or their equivalent linkage groups, which are well known to those of ordinary skill in the art, are chemically mimicked by the crosstalk inhibitors. However, various chemical substituents at each group are readily selected by those of ordinary skill in the art to create alternative crosstalk inhibitors.

The crosstalk inhibitors shown in FIGS. 1C and 1D are unbound or free inhibitors. It is also useful to provide such inhibitors in a bound format, for example, bound to BSA, where the alkyl acid group shown in FIGS. 1C and 1D are replaced with BSA or its equivalent. Examples of such bound inhibitors are shown in FIG. 1F.

EXAMPLE 1

Synthesis of N-[4(5-carboxypentylcarbamoyl)-cyclohexylmethyl Maleimide (CCM)

Succinimidyl 4-(N-maleimidomethyl) cyclohexane-1-carboxylate (SMCC, Pierce Chemical Co., Rockford, Ill.), (0.105 g, $3.14\times10^{-4}$ mol), 6-aminocaproic acid (0.041 g, $3.14\times10^{-4}$ mol) and pyridine (0.06 ml, $7.42\times10^{-4}$ mol) were dissolved in 6 ml dimethylformamide. The reaction was stirred at room temperature (generally about 20–25° C., the precise value is not important in this invention) for 4 hr, the resulting solution filtered on a fritted funnel, and solvents removed in vacuo. 4 ml 30 mM potassium phosphate, pH 3, was added to the white residue, and the pH lowered to 1.8 by dropwise addition of 1 N hydrochloric acid. The product was filtered on a fritted funnel, and washed with 30 mM potassium phosphate, pH 1.8. Finally, the product was dissolved in 15 ml methanol and the solvent removed in vacuo. 88 mg of the desired compound was recovered (see FIG. 1C).

EXAMPLE 2

Synthesis of Acetylthionpropionic Acid

To stirred solution of 3-mercaptopropionic acid (7 ml, 0.08 moles) and imidazole (5.4 g, 0.08 moles) in tetrahydrofuran (THF, 700 ml) was added dropwise over 15 minutes, under argon, a solution of 1-acetylimidazole (9.6 g, 0.087 moles) in THF (100 ml). The solution was allowed to stir a further 3 hours at room temperature after which time the THF was removed in vacuo. The residue was treated with ice-cold water (18 ml) and the resulting solution acidified with ice-cold concentrated HCl (14.5 ml) to pH 1.5–2. The mixture was extracted with water (2×50 ml), dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44–45° C.

EXAMPLE 3

Synthesis of N-methyl-(3-thioacetyl)propionamide

Acetylthiopropionic acid (0.5 g, $3.38\times10^{-3}$ mol, see Example 2), methylamine hydrochloride (0.25 g, $3.7\times10^{-3}$ mol) and pyridine (0.58 ml, $7.2\times10^{-3}$ mol) were dissolved in 15 ml anhydrous dimethylformamide. The reaction was started by addition of 1-ethyl-3-(3-dimethylaminopropyl)-carbodiimide hydrochloride (0.71 g, $3.7\times10^{-3}$ mol). The reaction was stirred over argon at room temperature for 5 hr. The solvents were removed in vacuo to afford a yellow oil. After addition of 5 ml water and 1 ml 0.5 M potassium phosphate, pH 7, to the oil, the pH of the solution was carefully adjusted to 7.0 with 10 N KOH. The aqueous solution was extracted 4 times, each with 25 ml methylene chloride. The organic phase was dried with anhydrous magnesium sulfate and filtered. The solvents were removed in vacuo, 10 ml ethyl alcohol was added to the residue, and the solvent was removed in vacuo to remove traces of pyridine. Ethyl acetate (1.5 ml) was added to the crystalline residue and the slight precipitate was filtered. The solvent was removed in vacuo and the compound was dried overnight in a vacuum desiccator. 0.43 g of the desired compound was recovered which melted at 67–70° C.

EXAMPLE 4

Synthesis of N-[4-(5-carboxypentylcarbamoyl)-cyclohexyl-methyl]-2-(methylcarbamoyl)-ethylthiosuccinimide (CCM-ATPMA)

The thiol ester of N-methyl-(3-thioacetyl)-propionamide (4.6 mg, $3.1 \times 10^{-5}$ mol, see Example 3) was hydrolyzed by the addition of 0.62 ml of 0.12 M KOH in 80% methanol. After 10 min, 0.3 ml of 0.5 M potassium phosphate, pH 7 was added to the thiol compound and the pH adjusted to 7.5 with 1 N hydrochloric acid. The thiol concentration was 34 mM (determined by reaction with dithionitrobenzoic acid, DTNB). SMCC-caproate (8.7 mg, $2.5 \times 10^{-5}$ mol) was dissolved in 0.4 ml of 0.5 M potassiumphosphate, pH 7.0, and the N-methyl-(3-mercapto)-propionamide solution (0.742 ml, $2.5 \times 10^{-5}$ mol) added. The solution was gassed with argon and the tube sealed. After 12 hr at room temperature, no thiol remained and the solvent was removed in vacuo. The residue was dissolved in 0.117 ml water to make a 213 mM solution of the desired compound (see FIG. 1D).

EXAMPLE 5

Synthesis of N-[4-(5-carboxypentylcarbamoyl)-cyclohexyl-methyl]-3-(methylcarbamoyl)-2-(carboxy)propyl Thio-succinimide (CCM-HCTLAM)

The thiol ester of N-acetylhomocysteine thiolactone (Aldrich Chemical Co., St. Louis, Mo.) (10 mg, $6.28 \times 10^{-5}$ mol) was hydrolyzed by dissolving the compound in 1.26 ml of 70% dimethylformamide/30% water and adding 0.032 ml 10 N potassium hydroxide. After 5 min, 0.3 ml of 0.5 M potassium phosphate, pH 7, was added to the thiol compound, and the pH adjusted to 7.5 with 1 N hydrochloric acid. The thiol concentration was 32 mM (determined by reaction with DTNB). SMCC-caproate (8.7 mg, $2.5 \times 10^{-5}$ mol) was dissolved in 0.4 ml of 0.5 M potassium phosphate, pH 7, and the N-acetylcysteine solution (0.781 ml, $2.5 \times 10^{-5}$ mol) added. The solution was gassed with argon, and the tube sealed. After 12 hr at room temperature, no thiol remained and the solvent was removed in vacuo. The residue was dissolved in 0.117 ml water to make a 213 mM solution of the desired compound (see FIG. 1D).

EXAMPLE 6

Synthesis of N-[4-(5-carboxypentylcarbamoyl)-cyclohexyl-methyl[-2-(carboxy)ethyl Thiosuccinimide (CCM-MPA)

SMCC-caproate (0.01 g, $2.86 \times 10^{-5}$ mol) was dissolved in 0.071 ml pyridine and 0.016 ml ($6.4 \times 10^{-6}$ mol) of the solution aliquoted into a test tube. Mercaptopropionic acid (0.0056 ml of 1.15 M solution in dimethylformamide, $6.4 \times 10^{-6}$ mol) was added to the tube, the solution gassed with argon, and the tube sealed. After 12 hr at room temperature, no thiol remained (as determined by reaction with DTNB) and the solvents were removed in vacuo. The residue was dissolved in 0.03 ml of 0.2 M potassium phosphate, pH 7, to make a 213 mM solution of the desired compound (see FIG. 1D).

EXAMPLE 7

Synthesis of N-[4-(5-carboxyventylcarbamoyl)-cyclohexyl-methyl]-2-(hydroxy)ethyl Thiosuccinimide (CCM-ME)

Mercaptoethanol (0.0045 ml of 1.43 M solution in dimethylformamide, $6.4 \times 10^{-6}$ mol) was added to SMCC-caproate (0.016 ml, $6.4 \times 10^{-6}$ mol) in pyridine (see Example 6). The solution was gassed with argon and the tube sealed. After 12 hr at room temperature, no thiol remained (as determined by reaction with DTNB) and the solvents were removed in vacuo. The residue was dissolved in 0.03 ml of 0.2 M potassium phosphate, pH 7, to make a 213 mM solution of the desired compound (see FIG. 1D).

EXAMPLE 8

Synthesis of Bis-(2-Hydroxyethylthio)succinimidyl Hexane (BMH-ME)

Bis-maleimidohexane (0.011 g, $3.98 \times 10^{-5}$ mol) and mercaptoethanol (0.0056 ml, $7.96 \times 10^{-5}$ mol) were dissolved in pyridine (0.22 ml). The reaction was stirred at 40° C. for 24 h. The solvent was removed in vacuo and the residue was dissolved in ethanol (5 ml) and the solvent removed in vacuo. This procedure was repeated 3 times more. The residue of the title compound weighed 16 mg.

EXAMPLE 9

Synthesis of Bis-(2-Acetylamino-2-Carboxyethylthio)succinimidyl Hexane (BMH-NAC)

Bis-maleimidohexane (0.05 g, $1.81 \times 10^{-4}$ mol) and N-acetylcysteine (0.059 g, $3.62 \times 10^{-4}$ mol) were dissolved in pyridine (1 ml). The reaction was stirred at 40° C. for 24 h. The solvent was removed in vacuo and the residue was dissolved in ethanol (5 ml) and the solvent removed in vacuo. This procedure was repeated 3 times more. The residue of the title compound weighed 0.1 g.

EXAMPLE 10

Synthesis of Bis-(2-Carboxythio)succinimidyl Hexane (BMH-MPA)

Bis-maleimidohexane (0.05 g, $1.81 \times 10^{-4}$ mol) and 3-mercaptopropionic acid (0.0315 ml, $3.62 \times 10^{-4}$ mol) were dissolved in dimethylformamide (1 ml) and then triethylamine (0.025 ml, $1.81 \times 10^{-4}$ mol) was added. The reaction was stirred at room temperature for 5 min. The solvent was removed in vacuo and the residue was dissolved in ethanol (5 ml) and the solvent removed in vacuo. This procedure was repeated 3 times more. The residue of the title compound weighed 0.1 g.

EXAMPLE 11

Synthesis of N,N'-Bis [3-(2-Hydroxyethylthiosuccinimidyl)propionyl]-2-Hydroxy-1,3-Propanedimine (BMP-ME N,N'-Bis-(3-maleimidopropionyl)-2-hydroxy-1,3-propanediamime (0.072 g, $1.83 \times 10^{-4}$ mol) and mercaptoethanol (0.025 ml, $3.67 \times 10^{-4}$ mol) were dissolved in dimethylformamide (1 ml) and then triethylamine (0.026 ml, $1.83 \times 10^{-4}$ Mol) was added. The reaction was stirred at room temperature for 5 min. The solvent was removed in vacuo and the residue was dissolved in ethanol (5 ml) and the solvent removed in vacuo. This procedure was repeated 3 times more. The residue of the title compound weighed 0.1 g.

EXAMPLE 12

Synthesis of Bis-(2-Carboxythio)succinimidyl Hexane (BMH-ME)

Bis-maleimidohexane (0.017 g, $6.2 \times 10^{-5}$ mol) and 3-mercaptopropionic acid methylamide (0.015 mg, $1.24 \times 10^{-6}$ mol) were dissolved in dimethylformamide (1.4 ml) and then triethylamine (0.009 ml, $6.2 \times 10^{-5}$ mol was added. The reaction was stirred at room temperature for 5 min. the solvent was removed in vacuo and the residue was dissolved in ethanol (5 ml) and the solvent removed in vacuo. The procedure was repeated 3 times more. The residue of the title compound weighed 0.02 g.

EXAMPLE 13

Synthesis of N,N'-Bis[3-(2-methylamidoethylthiosuccinimidyl)Propionyl]-2-Hydroxy-1,3-Propanediamine (BMP-MPAMA)

N,N'-Bis-(3-maleimidopropionyl)-2-hydroxy-1,3-propanediamine (0.024 g, $6.2 \times 10^{-5}$ mol) and 3-mercaptopropionic acid methylamide (0.015 mg, $1.24 \times 10^{-6}$ mol) were dissolved in dimethylformamide (1.4 ml) and then triethylamine (0.009 ml, $6.2 \times 10^{-5}$ mol) was added. The reaction was stirred at room temperature for 5 min. The solvent was removed in in vacuo and the residue was dissolved in ethanol (5 ml) and the solvent removed in vacuo. This procedure was repeated 3 times more. The residue of the title compound weighed 0.04 g.

EXAMPLE 14

Synthesis of 3-O-Carboxymethylmorphine Hydrochloride

Morphine sulfate (1.67 g, $5 \times 10^{-3}$ mol) was dissolved with potassium carbonate (2.07 g, $1.5 \times 10^{-2}$ mol) in 80 ml ethanol. The solution was heated to reflux while stirring and a solution containing bromoacetic acid (0.7 g, $5 \times 10^{-3}$ mol) added in 2 ml ethanol. This was refluxed for 2 hr, then the flask was cooled in an ice-water bath. The pH was adjusted to 3 with 12 N hydrochloric acid and precipitates were filtered. Solvents were evaporated under vacuum and 10 ml ethanol was added to the residue. Precipitates were filtered and solvents evaporated under vacuum. The residue was recrystallized from water/acetone (10:90). Approximately 300 mg of the desired product was recovered.

EXAMPLE 15

Synthesis of 3-O-[2-(2-Amino-4-Thiolbutanoic Acid Thio-lactone)Acetamidel-Morphine Hydrochloride (Morphine-HCTL)

Homocysteine thiolactone hydrochloride (120 mg, $7.8 \times 10^{-4}$ mol), 62 mg ($7.8 \times 10^{-4}$ mol) pyridine, and 296 mg ($7.8 \times 10^{-4}$ mol) 3-O-carboxymethyl morphine hydrochloride (see Example 14) were dissolved in 5 ml dimethylformamide. Addition of 1 ml of a dimethylformamide solution containing 177 mg ($8.6 \times 10^{-4}$ mol) dicyclohexylcarodiimide followed. The flask was purged with argon and the solution was stirred at 25° C. for 3 hr. The solvent was evaporated under vacuum and 20 ml water added to the residue. The solution was stirred for 5 min, then the insoluble dicyclohexylurea was filtered. The filtrate was washed with 10 ml methylene chloride. The pH of the aqueous layer was adjusted to 7 with an aqueous solution of saturated potassium carbonate. The aqueous solution was extracted 6 times with 10 ml methylene chloride. The combined organic extracts were dried with 2 g magnesium sulfate, filtered, and the solvent removed under vacuum. Ethanol (20 ml) was added to the residue and evaporated under vacuum to remove the pyridine. Ethyl acetate (10 ml) was added and insoluble precipitates were filtered. Ethereal hydrochloric acid (1 M) was added to the solution while stirring until the pH was red to litmus. The white solid was filtered and washed with ethyl acetate. The product was dried under vacuum with a yield of 316 mg.

EXAMPLE 16

Synthesis of p-Nitroamphetamine Hydrochloride d-Amphetamine sulfate (10 g, $2.7 \times 10^{-2}$ mol) was dissolved in sulfuric acid (5 mL) and the solution was cooled in an ice-water bath. Fuming nitric acid (4.6 mL) was added dropwise to the reaction solution. The reaction mixture was stirred on the ice-water bath for 1 h after which it was poured over ice-water. Sodium hydroxide (10 N) was added to adjust the solution to pH 12. The mixture was extracted with diethyl ether (2×100 mL), the combined organic layers were washed with water (2×100 mL) and were dried over anhydrous magnesium sulfate. The drying agent was removed by filtration and 1N ethereal hydrochloric acid was added to form the hydrochloride salt. The solvent was removed in vacuo. Acetone (200 mL) was added to the white residue and the suspension was stirred at room temperature for 2 h. The suspension was then filtered and the resulting white precipitate was recrystallized from ethanol/acetone to yield 3.5 g (60%) of p-nitroamphetamine hydrochloride as a white crystalline solid with a melting point of 191–192° C.

EXAMPLE 17

Synthesis of p-Aminoamphetamine Dihydrochloride p-Nitroamphetamine hydrochloride (3.5 g, $1.6 \times 10^{-4}$ mol, see Example 16) was dissolved in 200 ml methanol followed by the addition of 10% palladium-carbon (1.0 g) and ammonium formate (7.0 g). The reaction mixture was stirred at room temperature for 2 h. The catalyst was removed by filtration and the solvent evaporated in vacuo. The partially crystalline residue was dissolved in 20 ml water and potassium hydroxide pellets added to adjust the solution to pH 12. The solution was then extracted with methylene chloride (3×60 mL), the combined organic layers washed with water (1×50 mL) and dried over anhydrous magnesium sulfate. The drying agent was removed by filtration, and 1N ethereal hydrochloric acid added to form the hydrochloride salt. The solvent was removed in vacuo to give 2.0 g (56%) of p-aminoamphetamine dihydrochloride as a white crystalline solid with a melting point of 225–240° C.

EXAMPLE 18

Synthesis of p-Acetylthiopropionamide Amphetamine Hydrochloride [Amphetamine-ATP)

p-Aminoamphetamine dihydrochloride (2.0 g, $9 \times 10^{-3}$ mol, see Example 17) was dissolved in anhydrous dimethylformamide (88 mL). Acetylthiopropionic acid (1.5 g, $1.0 \times 10^{-2}$ mol) was added followed by anhydrous pyridine (2.4 mL, $2.97 \times 10^{-2}$ mol) and 1-(3-dimethylaminopropyl)-

3-ethylcarbodiimide hydrochloride (1.9 g, 1. 0×10² mol). The reaction mixture was stirred at room temperature for 1 h, and the solvent removed in vacuo. The residue was dissolved in water and washed with methylene chloride (3×50 mL), followed by the addition of 0.5 M potassium phosphate, pH 7 (100 mL). The aqueous solution was washed again with methylene chloride (3×50 mL). The solvent was removed in vacuo. Ethanol (2×50 ml) was added and removed in vacuo to azeotrope residual water. The dark yellow residue was triturated with methylene chloride (3×50 mL). Activated carbon (4.0 g) was added to the combined methylene chloride solution and stirred at room temperature for 30 min. The carbon was removed by filtration and the solvent evaporated in vacuo. The thick oil was redissolved in methylene chloride and acidified with 1 N ethereal hydrochloric acid. The methylene chloride/diethyl ether solution was decanted off and the residue was dried in vacuo to give 1.2 g of the desired compound as an orange crystalline solid.

EXAMPLE 19

Preparation of SMCC-Bovine Serum Albumin 10/1 (SMCC-BSA 10/1)

SMCC (17.5 mg, $5.2 \times 10^{-5}$ mol) in 0.87 ml acetonitrile was added to 17.5 ml of bovine serum albumin, BSA, (350 mg, $5.2 \times 10^{-6}$ mol) in 0.1 M potassium phosphate, 0.1 M potassium borate, 0.15 M sodium chloride, pH 7.5. The solution was stirred at room temperature for 1 hr and the pH maintained at 7–7.5 by addition of 1 N potassium hydroxide. The protein solution was applied to a 2.5 cm×25 cm column containing CELLUFINE GH25 resin (Amicon Corp.) equilibrated in 0.1 M potassium phosphate, 0.02 M potassium borate, 0.15 M sodium chloride, pH 7. 30 ml of SMCC-BSA was collected at 10.5 mg/ml. Analysis of the SMCC-BSA for maleimide groups, by reacting the protein with mercaptoethanol in slight excess over the estimated maleimide groups and measuring the unreacted mercaptoethanol by DTNB, showed that an average of 7 maleimide groups were attached to each BSA. The protein solution was frozen at −70° C.

EXAMPLE 20

Preparation of SMCC-Bovine Serum Albumin 15/1 (SMCC-BSA 15/1)

SMCC (49.2 mg, $1.5 \times 10^{-4}$ mol) in 2.46 ml acetonitrile was added in 2 portions at a 10 min interval to 30 ml of bovine serum albumin, BSA, (600 mg, $9 \times 10^{-6}$ mol) in 0.1 M potassium phosphate, 0.1 M potassium borate, 0.15 M sodium chloride, pH 7.5. The solution was stirred at room temperature for 1 hr. The protein solution was dialyzed with a PYROSTART ultrafiltration module (Sartorious, Gottingen) against 0.1 M potassium phosphate, 0.02 M potassium borate, 0.15 M sodium chloride, pH 7. 83 ml of SMCC-BSA was collected at 6 mg/ml. Analysis of the SMCC-BSA for maleimide groups, by reacting the protein with mercaptoethanol in slight excess over the estimated malelmide groups and measuring the unreacted mercaptoethanol by DTNB, showed that an average of 9 maleimide groups were attached to each BSA. The protein solution was frozen at −70° C.

EXAMPLE 21

Preparation of SMCC-Bovine Serum Albumin 50/1 (SMCC-BSA 50/1)

SMCC (7.5 mg, $2.2 \times 10^{-5}$ mol) in 0.37 ml acetonitrile was added to 2 ml of bovine serum albumin, BSA, (30 mg, $4.5 \times 10^{-7}$ mol) in 0.1 M potassium phosphate, 0.1 M potassium borate, 0.15 M sodium chloride, pH 8.0. The solution was stirred at room temperature for 1 hr. The protein solution was applied to a 1 cm×25 cm column containing CELLUFINE GH25 resin (Amicon Corp.) equilibrated in 0.1 M potassium phosphate, 0.02 M potassium borate, 0.15 M sodium chloride, pH 7. 5.2 ml of SMCC-BSA was collected at 5.23 mg/ml. Analysis of the SMCC-BSA for maleimide groups, by reacting the protein with mercaptoethanol in slight excess over the estimated maleimide groups and measuring the unreacted mercaptoethanol by DTNB, showed that an average of 30 maleimide groups were attached to each BSA. The protein solution was frozen at −70° C.

EXAMPLE 22

Preparation of Bovine Serum Albumin Crosstalk Inhibitors

The preparation of crosstalk inhibitors attached to BSA are described in this section. The SMCC-BSA derivatives, 10/1 (Example 19) and 50/1 (Example 21), were each used to make 4 different crosstalk inhibitors. The hydrolysis of the thiol esters of N-methyl-(3-thio-acetyl)propionamide and N-acetylhomocysteine thiolactone was as described in Examples 4 and 5, respectively. Stock solutions of mercaptopropionic acid (MPA) and mercaptoethanol (ME) were prepared in dimethylformamide at 1.15 M and 0.5 M, respectively. The thiol derivatives were added to the appropriate SMCC-BSA to produce the BSA crosstalk inhibitors as described in the table below. The thiol derivatives were reacted with the SMCC-BSA at room temperature for 4 hr. The protein solutions were each applied to a 1 cm×12 cm column containing CELLUFINE GH25 resin equilibrated in 0.1 M potassium phosphate, 0.02 M potassium borate, 0.15 M sodium chloride, pH 7. The crosstalk inhibitors prepared from the SMCC-BSA 10/1 were concentrated using CENTRICON ultrafiltration devices (Amicon Corp.). The final concentrations of the crosstalk inhibitors are listed in Table 1 below. The crosstalk inhibitor solutions were stored at 4° C.

TABLE 1

| SMCC-BSA | | THIOL DERIVATIVE | | CROSSTALK INHIBITOR | | |
|---|---|---|---|---|---|---|
| type | ml | mg | type | $\mu$mol | ml | ml | mg/ml |
| 1. 10/1 | 0.7 | 7.3 | HCTLAM | 1.8 | 0.035 | 0.44 | 15.0 |
| 2. 10/1 | 0.7 | 7.3 | ATPMA | 2.3 | 0.075 | 0.44 | 15.0 |
| 3. 10/1 | 0.7 | 7.3 | MPA | 2.9 | 0.003 | 0.41 | 16.1 |
| 4. 10/1 | 0.7 | 7.3 | ME | 2.5 | 0.005 | 0.44 | 15.0 |
| 5. 50/1 | 1.0 | 5.2 | HCTLAM | 7.0 | 0.14 | 2.5 | 1.9 |
| 6. 50/1 | 1.0 | 5.2 | ATPMA | 7.6 | 0.25 | 2.5 | 1.9 |
| 7. 50/1 | 1.0 | 5.2 | MPA | 11.5 | 0.01 | 2.3 | 2.0 |
| 8. 50/1 | 1.0 | 5.2 | ME | 10.0 | 0.02 | 2.9 | 1.6 |

EXAMPLE 23

Preparation of BSA-AMPHETAMINE

Amphetamine-ATP (0.095 g, $3 \times 10^{-4}$ mol, Example 18) was dissolved in 50 ml of 0.12 M potassium carbonate in 80% methanol/20% water. After 5 min at room temperature the thiol concentration was determined by reaction with DTNB to be 25 mM. The amphetamine thiol (7.6 ml, $1.9 \times 10^{-4}$ mol) was added with stirring to 20.3 ml (0.4 g, $5.9 \times 10^{-6}$ mol) of SMCC-BSA, 10/1. The pH of the solution was adjusted to 7 with 1 N hydrochloric acid. The container was purged with argon and the solution was stirred at room temperature for 2 hr. The conjugate solution was then dialyzed with a PYROSTART ultrafiltration module against 10 mM morpholineethanesulfonic acid, pH 5.77 and 110 ml of 3.57 mg/ml BSA-amphetamine was collected. The protein solution was frozen at −70° C.

EXAMPLE 24

Preparation of BSA-MORPHINE

Morphine-HCTL (0.068g, $1.3 \times 10^{-4}$ mol, Example 15) was dissolved in 5.7 ml of 70% dimethylformamide/30% water and 1.43 ml 1 N potassium hydroxide added. After 5 min the thiol concentration was determined by reaction with DTNB to be 16.9 mM. The morphine thiol (6.4 ml, $1.1 \times 10^{-4}$ mol) was added with stirring to 26.7 ml SMCC-BSA, 15/1, (0.16 g, $2.4 \times 10^{-6}$ mol). The container was purged with argon and the solution stirred at room temperature for 2 hr. The protein solution was then dialyzed using a PYROSART ultrafiltration module against 10 mM morpholineethanesulfonic acid, pH 5.77, and 29.5 ml of 5.39 mg/ml BSA-morphine collected. The protein solution was frozen at −70° C.

EXAMPLE 25

Preparation of Colloidal Gold Conjugates

Colloidal gold was first prepared by dissolving gold chloride trihydrate in deionized water (1.36 g in 0.7 liters) and filtering the solution through a 0.2μ filter. The filtered solution was added to round-bottom flask equipped with a heating mantle and the solution was heated to 85° C. A solution of trisodium citrate (2.54 g in 6.35 mL of deionized water) was added while stirring, and the solution held at 85° C. for 12 minutes before diluting it with 0.7 liters of deionized water at room temperature. Just prior to the adsorption of proteins to colloidal gold, one volume of 0.2 M (2-(N-morpholino) ethane sulfonic acid (MES), pH 5.77, was added to 19 volumes of colloidal gold and mixed.

Mixtures of BSA and ligand analogues coupled to BSA were adsorbed to colloidal gold to form conjugates by the following procedure. A mixture of BSA and BSA-amphetamine in 10 mM MES, pH 5.77, was prepared at a protein concentration of 6 mg/mL with the BSA-amphetamine representing 10% of the total protein in the mixture. A mixture of BSA and BSA-morphine was prepared at a protein concentration of 6 mg/mL with the BSA-morphine representing 20% of the total protein in the mixture. A mixture of BSA, BSA-amphetamine, and BSA-morphine was prepared at a protein concentration of 6 mg/mL with the BSA-amphetamine representing 10% and the BSA-morphine representing 20% of the total protein in the mixture. One volume of each protein mixture was mixed with 19 volumes of the colloidal gold solution in separate preparations. The preparations were allowed to stand for 30 minutes at room temperature. The conjugates were subjected to centrifugation at 40,000 g for 20 minutes at 22° C. to pellet the conjugate. The supernatant was removed and the pellet was washed twice with a volume of 50 mM potassium phosphate, 10 mM borate, pH 7.0, equal to the starting volume by resuspending it and subjecting it to centrifugation as described. After the final centrifugation, the soft part of the pellet was resuspended in approximately 0.5 ml of the buffer and stored at 4° C. The absorbances at 540 nm for the three conjugates were 78 for the 10% amphetamine conjugate, 103 for the 20% morphine conjugate, and 164 for the 10% amphetamine/20% morphine conjugate. The absorbance at 540 nm was used in characterizing the concentration of conjugate used in an assay.

EXAMPLE 26

Preparation of Amphetamine and Morphine Ligand Analogues Attached to Keyhole Limpet Hemocyanin (KLH), Bovine Serum Albumin (BSA), and Alkaline Phosphatase (AP)

KLM (6 ml of 14 mg/ml) was reacted with sulfosuccinimidyl 4-(N-maleimidomethyl)cyclohexane-1-carboxylate (SULFO-SMCC by adding 15 mg of SULFO-SMCC and maintaining the pH between 7 and 7.5 with 1N potassium hydroxide over a period of one hour at room temperature while stirring. The protein was separated from the unreacted SULFO-SMCC by gel filtration chromatography in 0.1 M potassium phosphate, 0.02 M potassium borate, and 0.15 M sodium chloride, pH 7.0, and 24 ml of KLH-maleimide collected at a concentration of 3.1 mg/ml. The free thiol of amphetamine and morphine ligand analogues (1.7 ml of 14 mM of 1.5 ml of 18 mM, respectively, see Examples 23 and 24) were each added to 6 ml of 3.1 mg/ml KLH-maleimide, the solutions stirred for 4 hours at 4° C., and then each dialyzed against 3 volumes of one liter each of pyrogen-free phosphate-buffered saline, pH 7.4, prior to immunization.

BSA (3.5 ml of 20 mg/ml) was reacted with SMCC by adding a solution of 6.7 mg of SMCC in 0.3 ml acetonitrile and stirring the solution for one hour at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. The free thiol form of amphetamine and morphine ligand analogues (0.17 ml of 14 mM and 0.15 ml of 18 mM, respectively) were each added to the BSA-maleimide (2 ml at 8.2 mg/ml), and the solutions stirred for 4 hours at 4° C. The solutions were used to coat microliter plates for the detection of antibodies that bind the amphetamine and morphine ligand analogues by standard techniques.

AP (1.5 ml of 10.9 mg/ml) was reacted with SULFO-SMCC by adding 3.1 mg of SULFO-SMCC to the solution and stirring at room temperature for one hour while maintaining the pH between 7.0 and 7.5 using 1 M potassium hydroxide. The protein was separated from the unreacted materials by gel filtration chromatography in 0.1 M potassium phosphate, 0.02 M potassium borate, 0.15 M sodium chloride, pH 7.0. The free thiol form of amphetamine and morphine ligand analogues (0.02 ml of 12 mM and 0.015 ml of 18 mM, respectively) were each added to the AP-maleimide (0.2 ml at 3.56 mg/ml), and the solutions stirred for 1.5 hours at 4° C. The protein was separated from unreacted materials by gel filtration chromatography in 0.1 M potassium phosphate, 0.02 M potassium borate, 0.15 M sodium chloride, pH 7.0, and the amphetamine and morphine ligand analogue conjugates diluted for use in assays.

EXAMPLE 27

Preparation of Latex-immobilized Affinity-purified Goat IgG Antibody Against the Fc Fragment of Mouse IgG Affinity-purified goat-anti-mouse Fc (BiosPacific) and polystyrene latex particles (sulfated, 1.07 μm,) (Interfacial Dynamics) were incubated separately at 45° C. for one hour, the antibody solution being buffered with 0.1 M 2-(N-morpholino) ethane sulfonic acid at pH 5.5. While vortexing the antibody solution, the suspension of latex particles was added to the antibody solution such that the final concentration of antibody was 0.3 mg/ml and the solution contained 1% latex solids. The suspension was incubated for 2 hours at 45° C. prior to centrifugation of the suspension to pellet the latex particles. The latex pellet was resuspended in 1% bovine serum albumin in phosphate-buffered-saline (PBS) and incubated for one hour at room temperature. Following centrifugation to pellet the latex, the pellet was washed three times by resuspension in PBS and centrifugation. The final pellet was resuspended in borate-buffered-saline, 0.1% sodium azide, pH 8.0, at a latex concentration of 1% solids. A 1% suspension of this latex preparation was capable of binding 40 µg/ml of monoclonal antibody.

EXAMPLE 28

Production and Primary Selection of Monoclonal Antibodies

Immunization of Balb/c mice was performed according to the method of Liu, D., Purssell, R., and Levy, J. G., Clin Chem, 5, 527–538 (1987). Fusions of spleen cells with SP2/0-Ag14 myeloma cells, propagation of hybridomas, and cloning were performed by standard techniques. Selection of hybridomas for further cloning began with culture supernatant at the 96-wellstage. A standard ELISA procedure was performed with amphetamine and morphine each attached to BSA adsorbed to the ELISA plate. Typically, a single fusion was plated out in twenty plates and approximately 10–20 wells per plate were positive by the ELISA assay. At this stage, a secondary selection could be performed if antibodies to the SMCC part of the linking arm were to be eliminated from further consideration. An ELISA assay using BSA derivatized with SMCC, but not containing the amphetamine or morphine derivatives, identified which of the positive clones that bound the BSA-drug ligand analogues were actually binding the SMCC-BSA. Depending on the particular objectives for the antibodies obtained, the antibodies specific for SMCC-BSA may be eliminated at this step.

EXAMPLE 29

Assay for the Selection of Antibodies Binding Amphetamine or Morphine Ligand Analoaue Conjugates with 100× Higher Affinity than their Affinity for Target Ligand Antibodies that are identified by the ELISA assay are subjected to further screening using the following assay method. Reaction mixtures containing 25 µl of an antibody dilution, 25 µl of diluent or an amphetamine or morphine standard, and 25 µl of amphetamine or morphine ligand analogue conjugated to alkaline phosphatase were each incubated for 20 minutes at room temperature in V-bottom microliter plates. A 25 µl volume of a 1% suspension of goat-antimouse IgG (Fc specific) adsorbed to latex was added to each reaction mixture and incubated another 10 minutes. The reaction mixtures were then subjected to centrifugation at 3000 rpm (1500 g) in a swinging bucket rotor. A 25 µl volume of the supernatant from each well was assayed for enzyme activity. By determining the enzyme activity in wells where high affinity antibody is in substantial excess over the amount needed to bind all of the immunoreactive conjugate, the enzyme activity that was associated with enzyme that did not contain bindable amphetamine or morphine ligand analogue was determined. This non-immunoreactive fraction of the activity of the supernatant was subtracted from the measured activity to determine the activity associated with the immunoreactive fraction. Initially high affinity antibodies were selected in this assay by serially diluting the antibody in the range from approximately 100 nM to below one nM antibody concentration in the reaction mixture while using approximately one nM of amphetamine or morphine ligand analogue conjugate. The free immunoreactive conjugate enzyme activity was determined by assaying the supernatant and the bound immunoreactive conjugate enzyme activity was determined by subtracting the free immunoreactive activity from the total immunoreactive conjugate enzyme activity. Under these conditions antibodies exhibiting a bound/free enzyme activity ratio of greater than 10 when the antibody is in excess over the conjugate are considered high affinity antibodies and are particularly preferred for the present invention.

EXAMPLE 30

Design of Crosstalk Inhibitors in Ligand Receptor Assays

The crosstalk inhibitors which are unattached to BSA (see Examples 4–13) and the ones which are attached to BSA (see Example 22) were synthesized because their structures resemble the linkage chemistry of the ligand analogue conjugates of amphetamine (Example 23) and morphine (Example 24). This can be seen by comparison of the chemical structures of the crosstalk inhibitors and the BSA conjugates (FIG. 1). Some of the crosstalk inhibitors resemble more closely the linkage chemistry than others. For example, the crosstalk inhibitors of ATPMA (Examples 4 and 22, #2 and #6) resemble most closely the linkage chemistry of the amphetamine-BSA conjugate (Example 23) compared to the others. The crosstalk inhibitors of HCT-LAM (Examples 5 and 22, #1 and #5) resemble most closely the linkage chemistry of the morphine-BSA conjugate (Example 24) compared to the others. The crosstalk inhibitors of MPA (Examples 6 and 22, #3 and #7) and of ME (Examples 7 and 22, #4 and #8) do not resemble the linkage chemistries as closely. Thus, in developing a strategy for the selection of potential crosstalk inhibitors, one should synthesize analogues of the linkage chemistry which resemble, very closely, the linkage chemistry, and others which do not. With a set of crosstalk inhibitors in hand, the effectiveness of each derivative should be tested and further modifications to the structure of the crosstalk inhibitors may be required to accomplish the desired response. For example, if one started with the crosstalk inhibitor of Examples 1 or 19 and the findings were that it was an ineffective crosstalk inhibitor (for example, it did not lower the response to the desired extent) then one would want to synthesize analogues which resemble more closely the linkage chemistry, such as the ones in Examples 4–13 and 22. Furthermore, the question of whether the crosstalk inhibitor is attached to a carrier molecule or is free in solution needs to be answered. The free crosstalk inhibitor will probably not be as effective in reducing a response as the attached crosstalk inhibitor. This is because the attached crosstalk inhibitor, if multiply attached to the carrier molecule, can compete multivalently with the ligand analogue conjugate and the free crosstalk inhibitor can only compete convalently. The degree of derivitization, or valency, of the carrier molecule is also important because the more highly derivatized carrier molecule will better compete with the ligand analogue conjugate and therefore will be more effective at reducing the undesirable interactions. The next examples give detailed experimental data relating to the issues discussed in this example.

Selection and Use of Crosstalk Inhibitors in Ligand Receptor Assays

EXAMPLE 31

The Effect of HCTLAM-BSA Concentration on the Amphetamine Crosstalk

Figure 2:
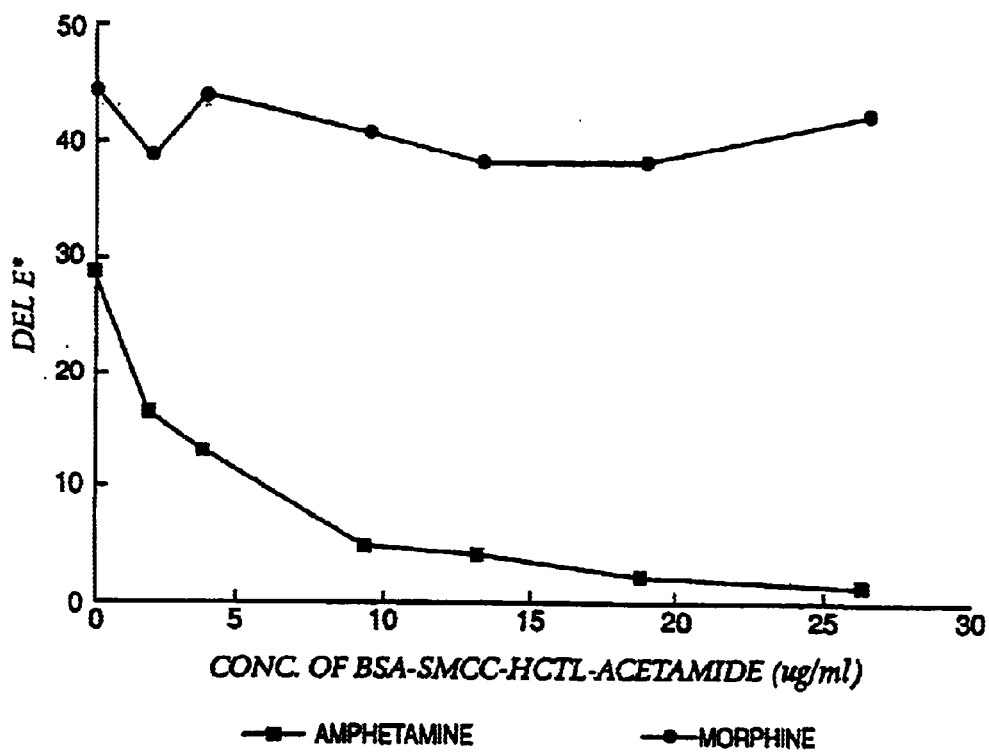

The effect of concentration of the HCTLAM-BSA crosstalk inhibitor on the amphetamine crosstalk was determined. Reaction mixtures were prepared by combining the following reagents: 10 μl of 0.5 M potassium phosphate, 0.1 M potassium borate, 0.75 M sodium chloride, 50 mg/ml BSA, pH 7 (hereafter referred to as "buffer"), 80 μl of urine, 4.85 μl of a 20% morphine colloidal gold conjugate (absorbance of 103 at 540 nm, this conjugate is hereafter referred to as morp conjugate) and 0, 1, 2, 5, 7, 10 and 14 μl of HCTLAM-BSA (Example 22, #5). The reaction mixtures were vortexed and each were applied to a nylon membrane onto which were bound monoclonal antibodies to amphetamine and morphine (hereafter referred to as amph Ab and morp Ab, respectively). The antibodies were bound to discrete zones of the nylon membrane by applying 2 μl of 2 mg/ml amph Ab and 2 μl of 20 mg/ml morp Ab, each in a pH 3.0 buffer. The affinities of the solid phase antibodies is greater for the ligand analogue of the ligand analogue conjugates than for the ligand and is the subject of co-pending U.S. patent application Ser. No. 583,046, filed Sep. 14, 1990, assigned to the same assignee as the present invention, and incorporated herein by reference. The reaction mixture was pulled through the membrane by a network of capillary channels which are the subject of copending U.S. patent application Ser. No. 500,299, filed Mar. 12, 1990, assigned to the same assignee as the present invention and hereby incorporated by reference herein. The membrane washed with a solution containing 50 mM potassium borate, 150 mM sodium chloride and 0.02% (v/v) Triton X-100, pH 8. The color density of the colloidal gold bound to the membrane at each discrete zone was measured with a Minolta CR241 reflectometer and the data is expressed in terms of Delta E* (referred to as DE* and De1E*), which is a measure of the minimum color difference that can be perceived by the human eye. In general, a DE* value of 2.5 or less is not visible to the human eye. A more complete description of this unit can be found in *Color in Business, Science and Industry* by D. B. Judd and G. Wyszecki, John Wiley and Sons. FIG. 2 shows the effect of HCTLAM-BSA on the crosstalk at the amphetamine zone. The data indicate that as the HCTLAMBSA concentration increases the response at the amphetamine zone decreases. In the absence of crosstalk inhibitor a substantial signal (29 DE*) was observed and was diminished by 19 μg of HCTLAM-BSA. The response at the morphine zone was essentially unchanged throughout the crosstalk inhibitor concentration range, suggesting that the crosstalk inhibitor did not substantially, or significantly, compete with the morphine conjugate for binding to the morp Ab.

EXAMPLE 32

The Effect of the Degree of Derivitization and Amount of Crosstalk Inhibitor-BSA on the Inhibition of Amphetamine and Morphine Crosstalk The experiments described in this example show the effect of derivitization of the crosstalk inhibitor-BSA conjugate on the inhibition of the amphetamine and morphine crosstalk.

Reaction mixtures were prepared by combining the following reagents: 10 μl of buffer, 80 μl of urine, either 4.8 μl of morp conjugate or 6.4 μl 10% amphetamine colloidal gold conjugate (absorbance of the stock solution at 560 nm is 78; this conjugate is referred to hereafter as amph conjugate) as indicated in Table 2, and crosstalk inhibitor-BSA (Example 22, #1–8) in amounts as described in Table 2. The reaction mixtures were each applied to a solid phase membrane onto which were bound amph Ab and morp Ab as described in Example 31. The membranes were washed and the color density quantified as described in Example 31. The results in Table 2 are expressed as DE* for each crosstalk inhibitor at the amph Ab and morp Ab zones.

TABLE 2

| | | CROSSTALK INHIBITOR-BSA | | | | |
|---|---|---|---|---|---|---|
| GOLD CONJ | DERIV | TYPE | μl | μl | DE*AMPH | DE*MORP |
| 1. Morp | | NONE | | | 28.2 | 44.3 |
| 2. Morp | 10/1 | HCTLAM | 1.8 | 27 | 27.2 | 44.3 |
| 3. Morp | 10/1 | ATPMA | 1.8 | 27 | 32.7 | 47.2 |
| 4. Morp | 10/1 | MPA | 1.8 | 28 | 33.8 | 48.1 |
| 5. Morp | 10/1 | ME | 1.8 | 27 | 32.3 | 42.5 |
| 6. Morp | 10/1 | HCTLAM | 12 | 180 | 18.9 | 41.1 |
| 7. Morp | 10/1 | ATPMA | 12 | 180 | 24.6 | 39.9 |
| 8. Morp | 10/1 | MPA | 12 | 190 | 22.7 | 42.0 |
| 9. Morp | 10/1 | ME | 12 | 180 | 21.7 | 41.1 |
| 10. Morp | 50/1 | HCTLAM | 14 | 26 | 2.2 | 47.1 |
| 11. Morp | 50/1 | ATPMA | 14 | 26 | 2.4 | 26.7 |
| 12. Morp | 50/1 | MPA | 14 | 29 | 0.1 | 31.2 |
| 13. Morp | 50/1 | ME | 14 | 23 | 1.6 | 42.6 |
| 14. Amph | | NONE | | | 48.0 | 4.5 |
| 15. Amph | 10/1 | HCTLAM | 12 | 180 | 38.4 | 2.5 |
| 16. Amph | 10/1 | ATPMA | 12 | 180 | 37.1 | 2.4 |
| 17. Amph | 10/1 | MPA | 12 | 190 | 34.5 | 2.3 |
| 18. Amph | 10/1 | ME | 12 | 180 | 36.9 | 1.5 |
| 19. Amph | 50/1 | HCTLAM | 14 | 26 | 23.2 | 0.9 |
| 20. Amph | 50/1 | ATPMA | 14 | 26 | 17.0 | 0.1 |
| 21. Amph | 50/1 | MPA | 14 | 29 | 17.0 | 0.1 |
| 22. Amph | 50/1 | ME | 14 | 26 | 19.0 | 1.6 |

These results show that the 10/1 crosstalk inhibitors at 27 μg/reaction mixture have essentially no effect on the amphetamine crosstalk (see 1–5 in Table 2). A higher mass of 10/1 crosstalk inhibitor (180–190 μg) had a slight effect on the amphetamine crosstalk (see 6–9 in Table 2), with the HCTLAM-BSA having the greatest effect. A possible reason for this effect of HCTLAM-BSA is that this crosstalk inhibitor most closely resembles the linkage chemistry of the morphine conjugate; therefore, the HCTLAM-BSA can best compete with the linkage chemistry of the morphine conjugate for binding to the amph Ab. Increasing the degree of derivitization of the BSA dramatically affects the crosstalk at the amph Ab zone (see 10–13 in Table 2). All crosstalk inhibitors at 50/1 diminished the response at the amph Ab zone. Thus, the degree of derivitization of the BSA (or carrier molecule) improves the potency of the crosstalk inhibitor because it can better compete, multivalently, with the ligand analogue conjugate for binding to the solid phase antibody.

In contrast to the morphine conjugate, the 10/1 crosstalk inhibitors have a more pronounced effect on the morphine crosstalk produced by the amphetamine conjugate (see 14–18 in Table 2). The 10/1 crosstalk inhibitors also have a slight effect on the amphetamine response. The 50/1 crosstalk inhibitors diminish the morphine crosstalk more than the 10/1 crosstalk inhibitors, but they also affect the amphetamine response (see 19–22 in Table 2). Thus, the 50/1 crosstalk inhibitors, in general, are more effective at decreasing both the amphetamine and morphine crosstalk than the 10/1. The 50/1 crosstalk inhibitors also decrease the response at the amphetamine Ab zone, but not to the extent that the specific signal is not observed. This is an example of an observable competition between inhibitor and a binding site which does not have a significant effect on the true positive result in the final assay. Indeed, such an inhibitor is useful in this invention since the assay still gives a true positive result with a lower number of false positive results.

The response at the amphetamine zone can be improved, if necessary, by increasing the antibody amount on the solid phase membrane. Thus, amphetamine Ab in a pH 3 buffer was immobilized at 2 mg/ml and at 15 mg/ml (as described in Example 25) and reaction mixtures were prepared containing 10 μl buffer, 80 μl urine containing 1500 ng/ml amphetamine, 0.2 μl of 14.2 mg/ml amphetamine Ab and 0 μl or 14 μl (26 μg) 50/1 HCTLAM-BSA. The reaction mixtures were contacted to the membrane onto which was bound the amph Ab at 2 and 15 mg/ml. After the reaction mixture passed through the membrane, the membrane was washed and the color density was measured as described in Example 31. In the absence of crosstalk inhibitor, the DE of the 2 and 15 mg/ml amph Ab zone was 32.1 and 49.5, respectively, and in the presence of crosstalk inhibitor the DE* was 6.4 and 24.8, respectively. Thus, the positive response can be increased with a higher amount of solid phase amph Ab.

EXAMPLE 33

The Effect of Unattached Crosstalk Inhibitors on the Amphetamine and Morphine Crosstalk This experiment describes the effectiveness of the unattached crosstalk inhibitors (Examples 4–13 on the amphetamine and morphine crosstalk. Reaction mixtures were prepared by combining the following reagents: 10 μl buffer, 80 μl urine, either 4.8 μl morphine conjugate or 6.4 μl amphetamine conjugate and crosstalk inhibitors (stock concentrations were 213 mM, examples 4–13) in amounts as indicated in Table 3. The reaction mixtures were contacted with a membrane onto which was mobilized amph Ab and Morp Ab, excess reagents were removed by washing and the color density measured, all as described in Example 31. The results are expressed as DE* for each crosstalk inhibitor at the amphetamine Ab and morp Ab zones.

TABLE 3

| | CROSSTALK INHIBITOR | | | | |
|---|---|---|---|---|---|
| GOLD CONJUGATE | TYPE | μl | μmol | DE*AMPH | DE*AMPH |
| 1. Morp | NONE | | | 28.8 | 44.2 |
| 2. Morp | CCM-HCTLAM | 2 | 0.43 | 16.5 | 40.2 |
| 3. Morp | CCM-HCTLAM | 5 | 1.1 | 10.0 | 37.3 |
| 4. Morp | CCM-ATPMA | 5 | 1.1 | 13.6 | 40.5 |
| 5. Morp | CCM-MPA | 2 | 0.43 | 25.5 | 43.5 |
| 6. Morp | CCM-MPA | 5 | 1.1 | 14.5 | 32.2 |
| 7. Morp | CCM-ME | 5 | 1.1 | 13.5 | 39.8 |
| 8. Amph | NONE | | | 42.0 | 5.1 |
| 9. Amph | CCM-HCTLAM | 2 | 0.43 | 36.9 | 4.4 |
| 10. Amph | CCM-ATPMA | 2 | 0.43 | 29.9 | 2.2 |
| 11. Amph | CCM-MPA | 2 | 0.43 | 33.1 | 5.1 |
| 12. Amph | CCM-ME | 2 | 0.43 | 33.2 | 2.7 |

The free crosstalk inhibitors decrease the amphetamine crosstalk without dramatically affecting the morphine response (see #1–7 in Table 3), except for the CCM-MPA compound, #6, which decreased the morphine response about 30%. The crosstalk inhibitors in #10 and #12 decreased the morphine response below the visual threshold, whereas the ones in #9 and #11 did not. The amphetamine response was affected in #10–12, but not dramatically. In general, the free or unattached crosstalk inhibitors are not as effective as the attached crosstalk inhibitors at inhibiting the amphetamine and morphine crosstalk (compare this example and Example 32). This is probably a result of the inability of the unattached crosstalk inhibitor to compete multivalently with the drug conjugate for the immobilized antibodies. This result can be improved simply by raising the concentration of the free inhibitor (compare 2 and 3 in Table 3).

EXAMPLE 34

Ligand Receptor Assay for Amphetamine and Morphine in a Sample

Ligand receptor assays were performed for amphetamine and morphine. The assays were performed in two formats: 1.

The ligand analogue conjugate in the reaction mixture is partially bound by antibody in the absence of ligand. 2. The ligand analogue conjugate in the reaction mixture is totally bound by antibody in the absence of ligand and up to the threshold concentration of ligand, as taught in U.S. Pat. Nos. 5,028,535 and 5,089,391.

Ligand Receptor Assay with Partially Bound Ligand Analogue Conjugate

Reaction mixtures were prepared by combining the following reagents: 10 μl buffer, 80 μl of urine containing 0,50,100,200, 400,600,1000,1500 ng/ml morphine sulfate, 3.0 μl of a 10% amphetamine/20% morphine colloidal gold conjugate (absorbance of 164 at 540 nm, this conjugate is hereafter referred to as amph/morp conjugate). The competition reaction was started by addition of 0.3 μl of 14.2 mg/ml amphetamine monoclonal antibody (amph ab) and 0.2 μl of 11.7 mg/ml morphine monoclonal antibody (morp Ab). At 5 min the reaction mixture was applied to a nylon membrane onto which were bound amph Ab and morp Ab as described in Example 31. The membrane was washed and the color density was quantified as described in Example 31. The data is expressed in terms of DE* as a function of drug concentration (see FIG. 3).

Figure 3:
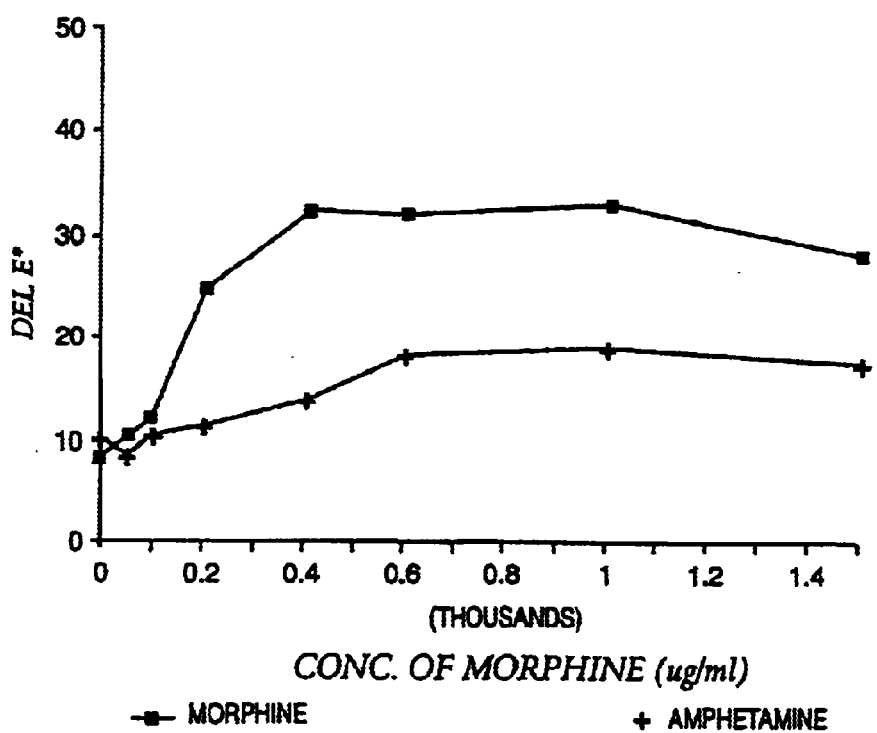

FIG. 3 shows that the color density of the morphine zone increases as a function of morphine in the sample. However, the color density of the amphetamine zone also increases as a function of morphine concentration. This crosstalk occurs because the solid phase amph Ab has an affinity for the morphine analogue of the morphine conjugate.

Figure 4:
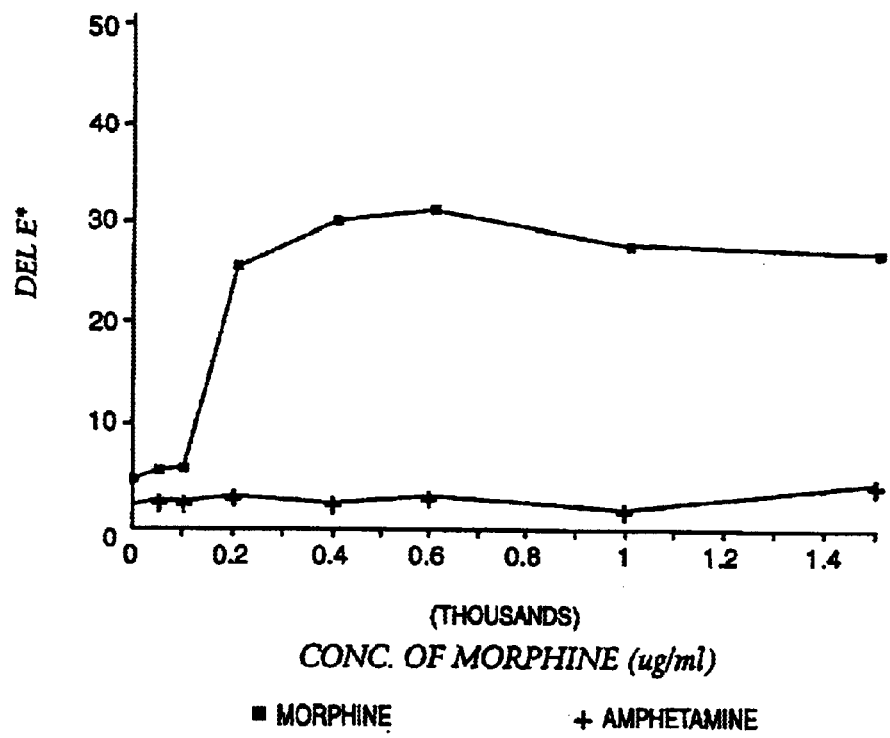

The effectiveness of the HCTLAM-BSA crosstalk inhibitor (Example 22, #5) at reducing the amphetamine crosstalk was tested by adding 14 μl of 1.9 mg/ml HCTLAM-BSA to the reaction mixtures, prepared as described above in this example. The assay was then performed and the results quantified as described above (see FIG. 4). FIG. 4 shows that the crosstalk inhibitor effectively reduced the binding of the morphine conjugate to the solid phase amphetamine zone. The morphine response was not affected by the crosstalk inhibitor. This is an example of the usefulness of crosstalk inhibitors in multiple ligand assays.

Ligand Receptor Assays with Totally Bound Ligand Analogue Conjugate up to the Threshold Concentration Reaction mixtures were prepared by combining the following reagents as taught by U.S. Pat. Nos. 5,028,535 and 5,089,391: 10 μl buffer, 80 μl of urine containing 0, 50, 100, 200, 400, 600, 1000, 1500 ng/ml morphine sulfate, 3.0 μl of a 10% amphetamine/20% morphine colloidal gold conjugate. The competition reaction was started by addition of 0.5 μl of 14.2 mg/ml amphetamine monoclonal antibody (amph Ab) and 1.1 μl of 11.7 mg/ml morphine monoclonal antibody (morp Ab). At 5 min the reaction mixture was applied to a nylon membrane onto which were bound amph Ab and morp Ab as described in Example 25. The membrane was washed and the color density was quantified as described in Example 31. The data is expressed in terms of DE as a function of drug concentration (see FIG. 5).

Figure 5:
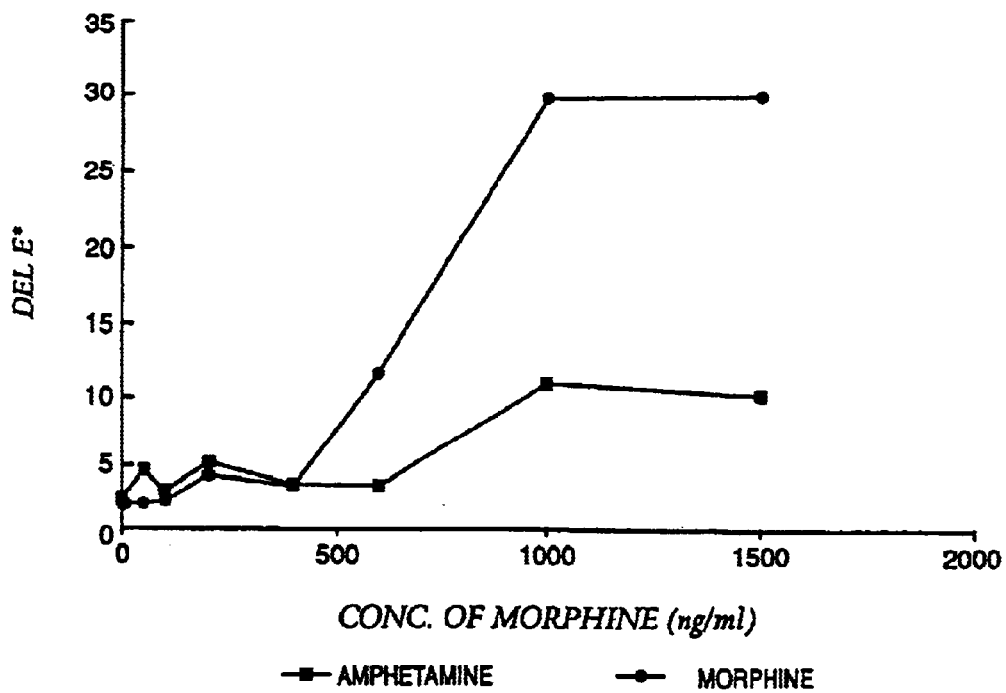

FIG. 5 shows that the color density of the morphine zone increases at the threshold concentration of 400 ng/ml. Also corresponding to the increase in the morphine response is the crosstalk amphetamine response, which is caused by the morphine conjugate binding to the amph Ab.

Figure 6:
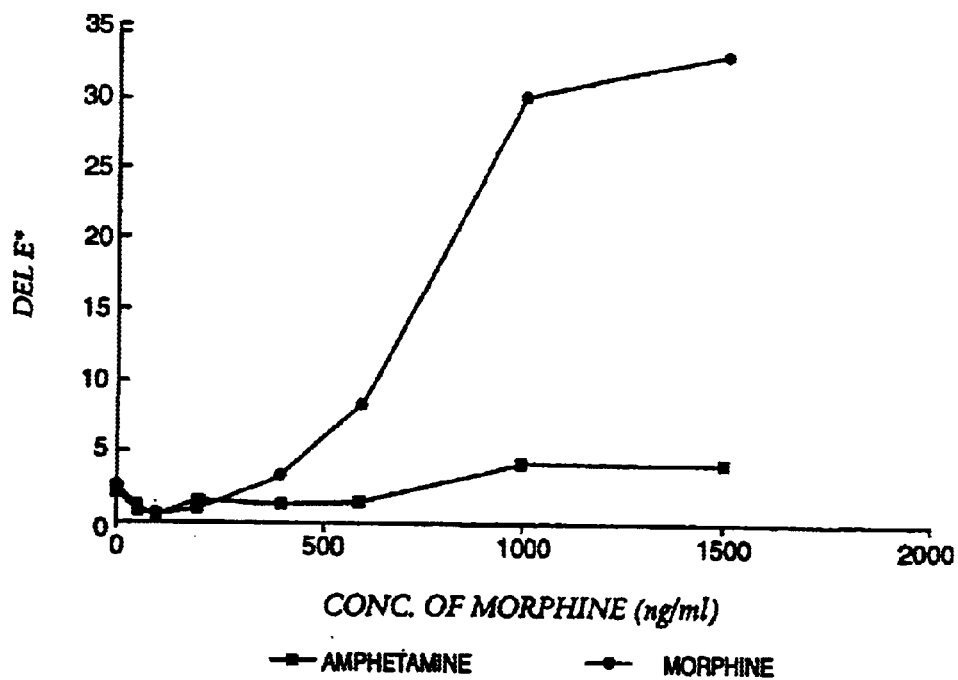

The effectiveness of the HCTLAM-BSA crosstalk inhibitor (Example 22, #5) at reducing the amphetamine crosstalk was tested by adding 14 μl of 1.9 mg/ml HCTLAM-BSA to the reaction mixtures, prepared as described above in this example. The assay was then performed and the results quantified as described above. FIG. 6 shows that the crosstalk inhibitor effectively reduced the binding of the morphine conjugate to the solid phase amphetamine zone. The morphine response was not affected by the crosstalk inhibitor. This is an example of the usefulness of crosstalk inhibitors in multiple ligand assays as taught by U.S. Pat. Nos. 5,028,535 and 5,089,391.

The effect of the HCTLAM-BSA crosstalk inhibitor on the morphine crosstalk was investigated. Reaction mixtures were prepared by combining the following reagents as taught by U.S. Pat. Nos. 5,028,535 and 5,089,391: 10 μl buffer, 80 μl of urine containing 0, 50, 100, 200, 400, 600, 1000, 1500 ng/ml d-amphetamine hydrochloride, 3.0 μl of a 10% amphetamine/20% morphine colloidal gold conjugate. The competition reaction was started by addition of 0.5 μl of 14.2 mg/ml amphetamine monoclonal antibody (amph Ab) and 1.1 μl of 11.7 mg/ml morphine monoclonal antibody (morp Ab). At 5 min the reaction mixture was applied to a nylon membrane onto which were bound amph Ab and morp Ab as described in Example 31. The membrane was washed and the color density was quantified as described in Example 31. The data is expressed in terms of DE* as a function of drug concentration (see FIG. 7).

Figure 7:
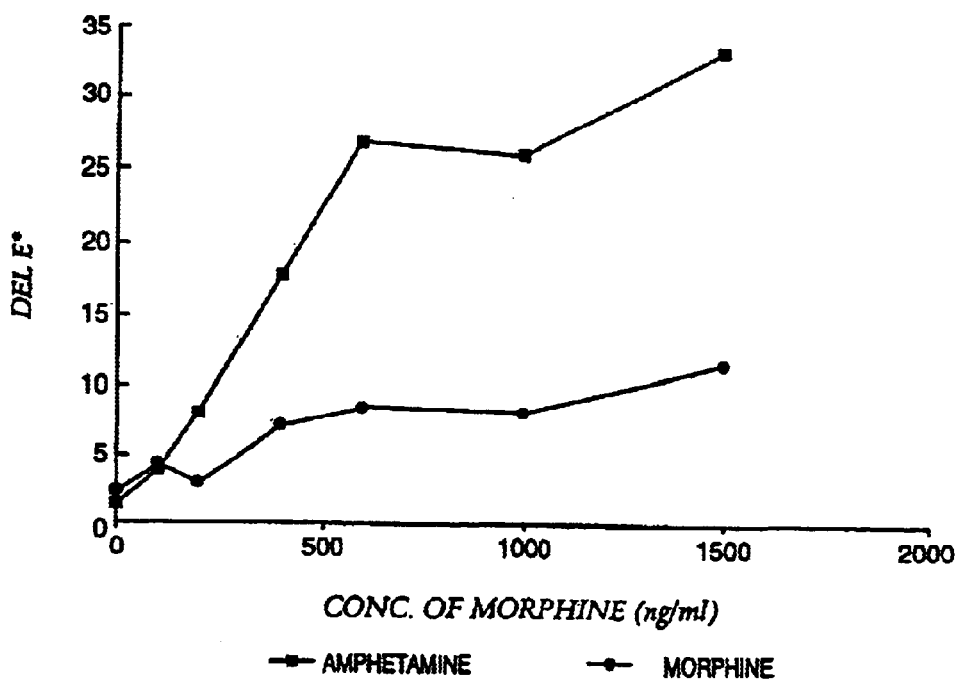

FIG. 7 shows that the color density of the amphetamine zone increases at the threshold concentration of 50 ng/ml. Also corresponding to the increase in the amphetamine response is the crosstalk morphine response, which is caused by the amphetamine conjugate binding to the morp Ab.

Figure 8:
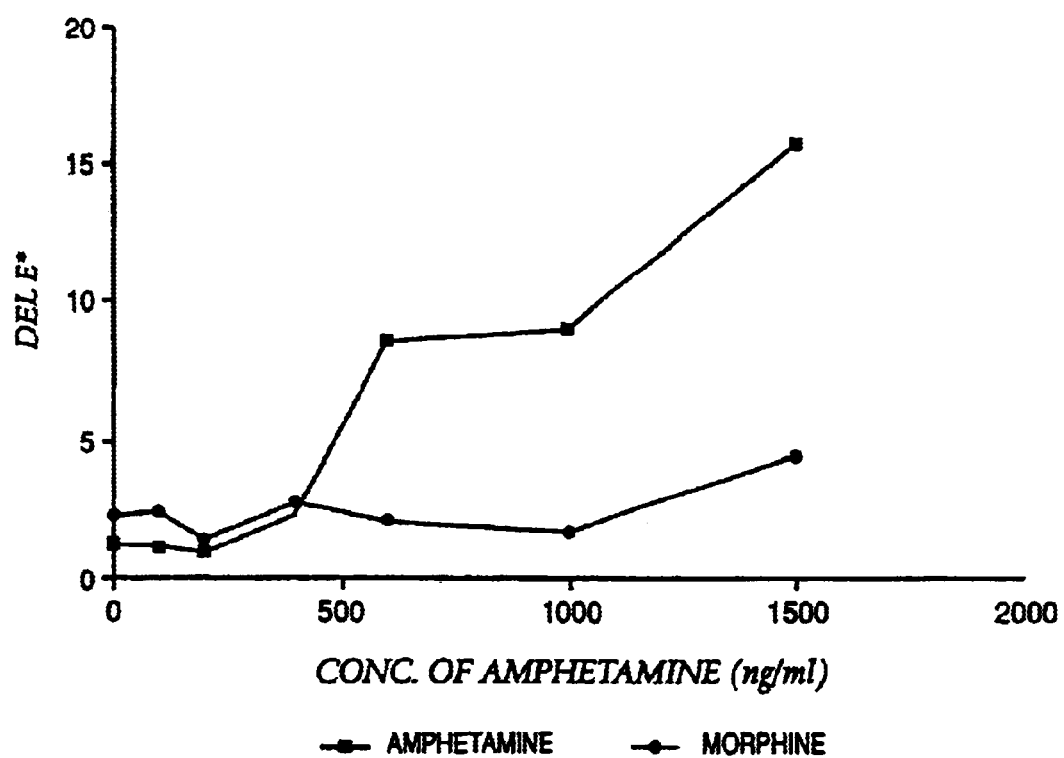

The effectiveness of the HCTLAM-BSA crosstalk inhibitor (Example 22, #5) at reducing the morphine crosstalk was tested by adding 14 μl of 1.9 mg/ml HCTLAM-BSA to the reaction mixtures, prepared as described above in this example. The assay was then performed and the results quantified as described above. FIG. 8 shows that the crosstalk inhibitor effectively reduced the binding of the amphetamine conjugate to the solid phase morphine zone. The amphetamine response was decreased by the crosstalk inhibitor and in this example it changed the value of the threshold concentration of amphetamine from 50 ng/ml to 400 ng/ml. The potential for a change in the threshold concentration by crosstalk inhibitors must be recognized when developing assays. This is an example of the usefulness of crosstalk inhibitors in multiple ligand assays as taught by U.S. Pat. Nos. 5,028,535 and 5,089,391.

Other embodiments are within the following claims.

What is claimed is:

1. A composition of matter comprising:

(a) a plurality of different ligand analogue conjugates each different ligand analogue conjugate corresponding to a one of a plurality of different target ligands, wherein each ligand analogue conjugate comprises a binding site for an antibody or a ligand receptor produced by a standard immunologic technique, and wherein each ligand analogue conjugate is attached via a linkage site to a protein, polypeptide, polymer, or a signal development element, said linkage site being the same or different from the linkage site of the other ligand analogue conjugates; and (b) at least one crosstalk inhibitor comprising an analogue of at least one linkage site present amongst the plurality of different ligand analogue conjugates, wherein the crosstalk inhibitor is present in an amount sufficient to inhibit binding of the linkage site of at least one ligand analogue conjugate in a ligand receptor assay to an antibody or ligand receptor produced by a standard immunologic technique.

drug of abuse, a metabolite of a drug of abuse, an analogue of a drug of abuse, an analogue of a metabolite of a drug of abuse, a therapeutic drug, a metabolite of a therapeutic drug, an analogue of a therapeutic drug, and an analogue of a metabolite of a therapeutic drug.

6. A composition of matter comprising:
(a) a ligand analog conjugate of the formula

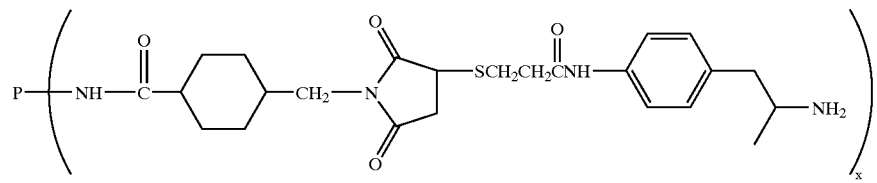

2. A composition for use in an assay for determining the amount or presence of a target ligand, wherein the target ligand is a binding partner to a ligand receptor, the composition comprising:
(a) a ligand analogue conjugate comprising a binding site for a receptor attached via a linkage site to a protein, polypeptide, polymer, or signal development element;
(b) a ligand receptor comprising an antibody or a fragment thereof which specifically binds the ligand analogue conjugate; and
(c) a crosstalk inhibitor comprising at least one analogue of the linkage site in an amount sufficient to inhibit binding of the ligand receptor to the linkage site.

3. A composition comprising:
(a) a ligand analogue conjugate $P\text{-}(Z\text{-}L)_x$, wherein P is a protein, polypeptide, polymer, or signal development element, wherein x is between 1 and 200, wherein L is a ligand analog, and wherein Z is an aliphatic or aromatic linkage site of from 1–50 carbon atoms and 0–20 heteroatoms selected from the group consisting of N, O, and S;
(b) a ligand receptor comprising an antibody or a fragment thereof which specifically binds the ligand analogue conjugate; and
(c) a crosstalk inhibitor Z' comprising an analogue of Z in an amount sufficient to inhibit binding of the ligand receptor to the linkage site.

4. A composition comprising:
(a) a ligand analogue conjugate $P\text{-}(Z\text{-}L)_x$, wherein P is a protein, polypeptide, polymer, or signal development element, wherein x is between 1 and 200, wherein L is a ligand analog, and wherein Z is an aliphatic or aromatic linkage site of from 1–50 carbon atoms and 0–20 heteroatoms selected from the group consisting of N, O, and S;
(b) a ligand receptor comprising an antibody or a fragment thereof which specifically binds the ligand analogue conjugate; and
(c) a crosstalk inhibitor $P\text{-}(Z')_x$, in an amount sufficient to inhibit binding of Z to the ligand receptor, wherein P is a protein, polypeptide, polymer, or signal development element, wherein x is between 1 and 200, and wherein Z' is an analogue of Z.

5. A composition according to claim 3 or 4, wherein ligand analogue L is selected from the group consisting of a wherein P is protein, polypeptide, polymer, or a means for signal development, and wherein x is between 1 and 50;

(b) a crosstalk inhibitor of the formula

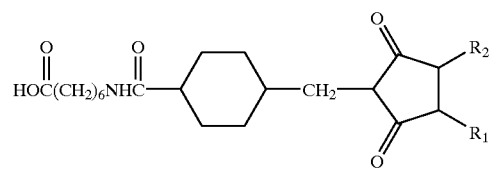

wherein, when $R_1$ is H, then $R_2$ is H;

when $R_1$ is

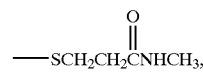

then $R_2$ is H;

when $R_1$ is

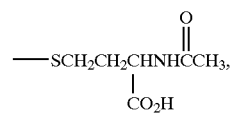

then $R_2$ is H;

when $R_1$ is

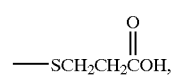

then $R_2$ is H;

when $R_1$ is $-SCH_2CH_2OH$, then $R_2$ is H;

whereby the composition inhibits crosstalk.

7. A composition of matter comprising:
(a) a ligand analogue conjugate of the formula

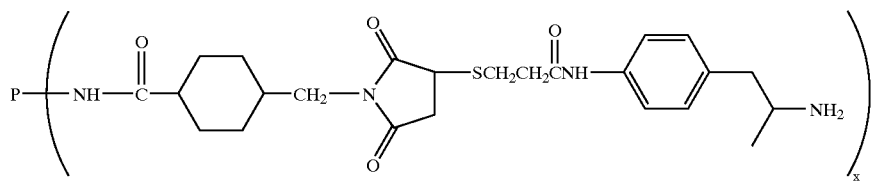

wherein P is a protein, polypeptide, polymer, or a means for signal development, and wherein x is between 1 and 50; and (b) a crosstalk inhibitor selected from the group consisting of

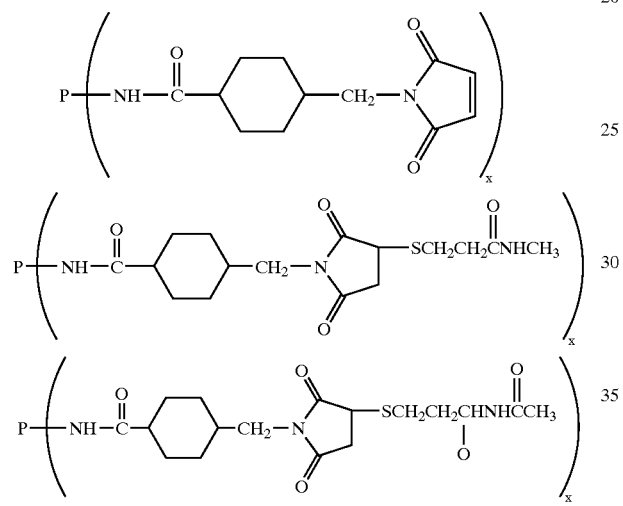

-continued

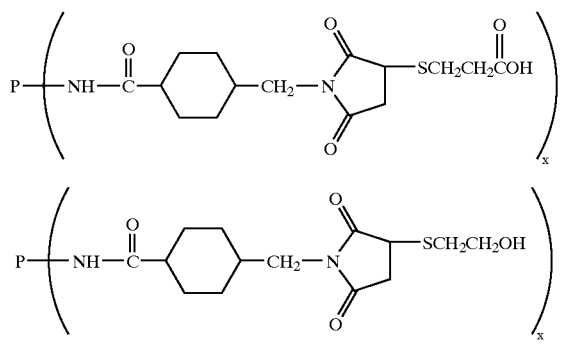

wherein P is a protein polypeptide, polymer, or complex comprising at least two molecules, and wherein x is between 1 and 50;

wherein the composition inhibits crosstalk.

8. A composition of matter comprising:
(a) a ligand analogue conjugate of the formula

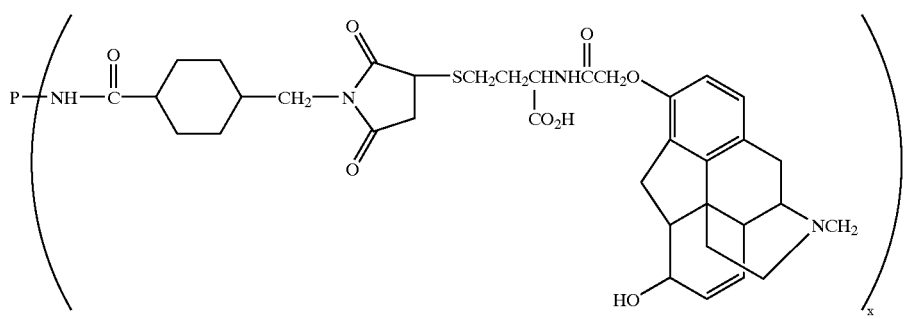

wherein P is a protein, polypeptide, polymer, or a means for signal development, and wherein x is between 1 and 50; and
(b) a crosstalk inhibitor of the formula

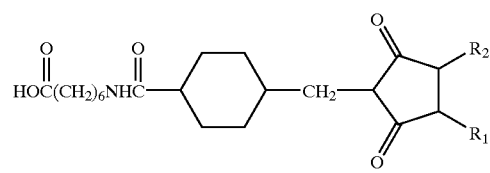

wherein, when $R_1$ is H, then $R_2$ is H;
when $R_1$ is $$-SCH_2CH_2\overset{O}{\overset{\|}{C}}NHCH_3,$$

then R2 is H;
when $R_1$ is $$-SCH_2CH_2\underset{CO_2H}{\overset{}{C}}HNH\overset{O}{\overset{\|}{C}}CH_3,$$

then $R_2$ is H;
when $R_1$ is
then $R_2$ is H;
when $R_1$ is $$-SCH_2CH_2\overset{O}{\overset{\|}{C}}OH,$$

then $R_2$ is H;
when $R_1$ is —$SCH_2CH_2OH$, then $R_2$ is H;
whereby the composition inhibits crosstalk.

9. A composition of matter comprising:
(a) a ligand analogue conjugate of the formula

[chemical structure with P—NH—C(O)—cyclohexyl—CH₂—N(maleimide)—SCH₂CH₂CHNHCCH₂O—morphine derivative, CO₂H]

wherein P is a protein, polypeptide, polymer, or a means for signal development, and wherein x is between 1 and 50; and (b) a crosstalk inhibitor selected from the group consisting of

[chemical structure P—NH—C(O)—cyclohexyl—CH₂—N(maleimide)]ₓ

[chemical structure P—NH—C(O)—cyclohexyl—CH₂—N(succinimide)—SCH₂CH₂CNHCH₃]ₓ

[chemical structure P—NH—C(O)—cyclohexyl—CH₂—N(succinimide)—SCH₂CH₂CHNHCCH₃, O]ₓ

[chemical structure P—NH—C(O)—cyclohexyl—CH₂—N(succinimide)—SCH₂CH₂COH]ₓ

[chemical structure P—NH—C(O)—cyclohexyl—CH₂—N(succinimide)—SCH₂CH₂OH]ₓ wherein P is a protein polypeptide, polymer, or complex comprising at least two molecules, and wherein x is between 1 and 50;

whereby the composition inhibits crosstalk.

10. A composition of matter comprising:

(a) a ligand analogue conjugate of the formula

[chemical structure P—NH—C(O)—cyclohexyl—CH₂—N(succinimide)—SCH₂CH₂CNH—R]ₓ wherein R is a ligand analogue, and wherein P is a protein, polypeptide, polymer, or a means for signal development, and wherein x is between 1 and 50; and (b) a crosstalk inhibitor selected from the group consisting of

[Structural formula: P—(NH—C(=O)—C6H10—CH2—N(maleimide))x]

[Structural formula: P—(NH—C(=O)—C6H10—CH2—N(succinimide)—SCH2CH2C(=O)NHCH3)x]

[Structural formula: P—(NH—C(=O)—C6H10—CH2—N(succinimide)—SCH2CH2CHNHC(=O)CH3, with O substituent)x]

[Structural formula: P—(NH—C(=O)—C6H10—CH2—N(succinimide)—SCH2CH2COH)x]

[Structural formula: P—(NH—C(=O)—C6H10—CH2—N(succinimide)—SCH2CH2OH)x]

wherein P is a protein polypeptide, polymer, or complex comprising at least two molecules, and wherein x is between 1 and 50;

whereby the composition inhibits crosstalk.

11. A composition of matter comprising:

(a) a ligand analogue conjugate of the formula

[Structural formula: P—(NH—C(=O)—C6H10—CH2—N(succinimide)—SCH2CH2CHNHC(=O)CH2—R, with CO2H substituent)x]

wherein R is a ligand analogue, and wherein P is a protein, polypeptide, polymer, or a means for signal development, and wherein x is between 1 and 50; and (b) a crosstalk inhibitor selected from the group consisting of

[Structural formula: P—(NH—C(=O)—C6H10—CH2—N(maleimide))x]

[Structural formula: P—(NH—C(=O)—C6H10—CH2—N(succinimide)—SCH2CH2C(=O)NHCH3)x]

[Structural formula: P—(NH—C(=O)—C6H10—CH2—N(succinimide)—SCH2CH2CHNHC(=O)CH3, with O substituent)x]

[Structural formula: P—(NH—C(=O)—C6H10—CH2—N(succinimide)—SCH2CH2COH)x]

[Structural formula: P—(NH—C(=O)—C6H10—CH2—N(succinimide)—SCH2CH2OH)x]

wherein P is a protein polypeptide, polymer, or complex comprising at least two molecules, and wherein x is between 1 and 50, whereby the composition inhibits crosstalk.

* * * * *

UNITED STATES PATENT AND TRADEMARK OFFICE
CERTIFICATE OF CORRECTION

| | |
|---|---|
| PATENT NO. | : 6,777,190 B1 |
| DATED | : August 17, 2004 |
| INVENTOR(S) | : Kenneth F. Buechler et al. |

It is certified that error appears in the above-identified patent and that said Letters Patent is hereby corrected as shown below:

<u>Column 34,</u>
Line 58, replace "corresponding to a" with -- corresponding to --

Signed and Sealed this

Eighth Day of February, 2005

JON W. DUDAS
*Director of the United States Patent and Trademark Office*